(12) United States Patent
Pace et al.

(10) Patent No.: US 6,726,919 B2
(45) Date of Patent: Apr. 27, 2004

(54) INJECTABLE DISPERSION OF PROPOFOL

(75) Inventors: Gary W. Pace, Winchester, MA (US); Michael G. Vachon, Quebec (CA); Awadesh K. Mishra, Quebec (CA); Robert A. Snow, West Chester, PA (US)

(73) Assignee: RTP Pharma, Inc., Durham, NC (US)

( * ) Notice: Subject to any disclaimer, the term of this patent is extended or adjusted under 35 U.S.C. 154(b) by 0 days.

(21) Appl. No.: 09/880,104

(22) Filed: Jun. 14, 2001

(65) Prior Publication Data

US 2002/0022667 A1 Feb. 21, 2002

Related U.S. Application Data

(60) Provisional application No. 60/211,977, filed on Jun. 16, 2000.

(51) Int. Cl.[7] .................................. A61F 13/00
(52) U.S. Cl. ....................... 424/422; 424/451; 424/489; 424/642; 424/643; 514/487; 514/731
(58) Field of Search ................. 514/487, 731; 424/489, 451, 422, 642, 643

(56) References Cited

U.S. PATENT DOCUMENTS 6,267,985 B1 * 7/2001 Chen et al. ................. 424/451

FOREIGN PATENT DOCUMENTS

GB 2298789 * 9/1996

* cited by examiner

*Primary Examiner*—Thurman K. Page
*Assistant Examiner*—Charesse Evans
(74) *Attorney, Agent, or Firm*—Edwards & Angell, LLP

(57) ABSTRACT

A sterile, injectable homogenized dispersion of micromatrices or microdroplets having a mean diameter from about 50 nm to about 1000 nm comprising about 1% to about 7.5% of propofol, about 1% to about 8% of a propofol-soluble diluent, and about 0.67% to about 5% of a surface stabilizing amphiphilic agent suspended in an aqueous medium containing a synergetic quantity of antimicrobial agent and a tonicity modifying amount of a pharmaceutically acceptable water-soluble hydroxyl-group-containing excipient, wherein the ratio of propofol to diluent is in the range of about 0.25 to about 7.5 while the ratio of propofol to amphiphilic agent is in the range from about 0.4 to about 1.5, and wherein the viscosity of the dispersion is in the range of 1.1 to 8 cps, processes for the formation of the dispersion, and methods of use are disclosed.

48 Claims, No Drawings

INJECTABLE DISPERSION OF PROPOFOL

This application claims the benefit of Provisional Application No. 60/211,977, filed Jun. 16, 2000, the entire content of which is hereby incorporated by reference in this application.

This invention relates to processes and compositions and methods of use of formulations containing propofol (2,6-diisopropylphenol) and one or more antimicrobial agent.

BACKGROUND

Formulations containing propofol for injection can be used in clinical settings for production and maintenance of ambulatory anesthesia, neurosurgical anesthesia, neuroanesthesia, pediatric anesthesia, monitored anesthesia care (MAC) sedation, intensive care (ICU) sedation, cardiac anesthesia, and in other clinical situations (see for example, Smith, I., White, P. F., Nathanson, M. and Gouldson, R. (1994) "Propofol—An update on its clinical use," Anesthesiology, 81, 1005–1043).

U.S. Pat. Nos. 4,056,635 and 4,452,817 disclose compositions containing propofol suitable for parenteral administration to produce anesthesia in warm-blooded animals as mixtures of propofol with surfactants such as CREMOPHOR-RH40™, CREMOPHOR-EL™, and TWEEN-8 ™ in an aqueous medium that may also contain ethanol or other pharmaceutically acceptable ingredients.

U.S. Pat. No. 4,798,846 discloses sterile propofol compositions containing 1% to 2% propofol alone or dissolved in oil such as arachis oil or ethyl oleate. These formulations are stabilized with surfactants.

A propofol preparation for clinical use is commercially available as DIPRIVAN® 1% Injection. This contains propofol dissolved in soybean oil as an emulsion stabilized with egg lecithin in water. Each milliliter of this formulation consists of 10 mg/mL of propofol, 100 mg/mL of soybean oil, 22.5 mg/mL of glycerol, 12mg/mL of egg lecithin, and disodium edetate (0.005%). This product formulation requires strict aseptic technique during handling, and a vial of the product can be used only once because of the ease of microbial contamination in a clinical use setting.

Incidences of serious infection in human subjects have been linked to the use of DIPRIVAN. For example, see Nichols, R. L. and Smith, J. W. (1995) "Bacterial Contamination of an Anesthetic Agent," New Eng. J. Med., 333(3), 184–185; Tessler, M., Dascal, A., Gioseffini, S., Miller, M. and Mendelson, J. (1992) "Growth curves of *Staphyloccoccus aureus, Candida albicans* and *Moraxella osloensis* in propofol and other media," Can. J. Anaesth. 39(5), 509–511; Ardulno, M. J., Bland, L. A., McAllister, S. K., Aguero, S. M., Villarino, M. E., McNeil, M. M., Jarvis, W. R. and Favero, M. S. (1991) "Microbial Growth and Endotoxin Production in the Intravenous Anesthetic Propofol," Inf. Control Hosp. Epidem., 12(9), 535–539; Sosis, M. B. and Braverman, B. (1993) "Growth of *Staphylococcus aureus* in Four Intravenous Anesthetics," Anesth. Anal. 77, 766–768; Sosis, M. B., Braverman, B. and Villaflor, E. (1995) "Propofol, but not Thiopental, Supports the Growth of *Candida albicans*," Anesth. Anal. 81, 132–134; Crowther, J., Hrazdil, J., Jolly, D. T., Galbraith, J. C., Greacen, M. and Grace, M. (1996) "Growth of Microorganisms in Propofol, Thiopental and a 1:1 Mixture of Propofol and Thiopental," Anesth. Anal. 82, 475–478; and Center for Disease Control report, New England Journal of Medicine (1995) Vol. 333, No 3, pp 184–5 and the accompanying editorial in the same issue.

DIPRIVAN can exhibit a thrombogenic potential in clinical use. Symptoms span the range of thrombosis and phlebitis and include incidences of burning, stinging or sensations of pain (see Physicians Desk Reference 1999, page 3416).

U.S. Pat. Nos. 5,714,520, 5,731,355 and 5,731,356 disclose propofol formulations containing disodium edetate as a preservative in amounts sufficient to prevent no more microbial growth than a 10-fold increase over 24 hours after adventitious extrinsic contamination with the microorganisms *Staphylococcus aureus* ATCC 6538, *Escherichia coli* ATCC 8739, *Pseudomonas aeruginosa* ATCC 9027 and *Candida albicans* ATCC 10231. However, this formulation is not considered to be an antimicrobially preserved product under USP standards as exemplified in Sklar, G. E. (1997) "Propofol and postoperative infections," Ann Pharmacother, 31, 1521–3. Edetate may not be effective as a preservative against growth of microorganisms in a DIPRIVAN formulation if challenged by organisms other than those cited above or by higher loads of organisms, i.e., exceeding 100 CFU/mL.

U.S. Pat. No. 6,140,374 discloses the use of a number of antimicrobial agents in propofol containing oil-in-water emulsions including combinations of edetate and benzyl alcohol.

U.S. Pat. No. 6,028,108 discloses a sterile oil-in-water emulsion of propofol and an amount of pentetate sufficient to prevent significant growth of microorganisms for at least 24 hours after adventitious extrinsic contamination.

U.S. Pat. No. 6,177,477 discloses a sterile oil-in-water emulsion of propofol and an amount of tromethamine (TRIS) sufficient to prevent significant growth of microorganisms for at least 24 hours after adventitious extrinsic contamination.

U.S. Pat. No. 6,147,122 discloses a sterile oil-in-water emulsion of propofol and an amount of sulfite sufficient to prevent significant growth of microorganisms for at least 24 hours after adventitious contamination.

Pain on injection of commercial formulations of propofol has been reported to occur in many patients; for example, see Mirakhur, R. K. (1988) "Induction characteristics of propofol in children: Comparison with thiopentone," Anesthesia, 43, 593–598; Stark, R. D., Binks, S. M., Dukta, V. N., O'Connor, K. M., Arnstein, M. J. A., Glen, J. B. (1985) "A review of the safety and tolerance of propofol ('Diprivan')," Postgrad. Med. J., 61 S, 152–156; and Mangar, D. and Holak, E. J. (1992) "Tourniquet at 50 mm Hg followed by intravenous lidocain diminishes hand pain associated with propofol injection," Anesth. Analg., 74, 250–252. Even with a low dose of propofol administered for sedation, the incidence of pain can be high; for example, see White, P. F. and Negus, J. B. (1991) "Sedative infusions during local and regional anesthesia: A comparison of midazolam and propofol," J. Clin. Anesth., 3, 32–39; and Ghouri, A. F., Ramirez Ruiz, M. A., and White, P. F. (1994) "Effect of flumazenil on recovery after midazolam and propofol sedation," Anesthesiology, 81, 333–339.

The mechanism or mechanisms responsible for venous pain on propofol administration are unknown. No measurable reduction in pain was detected clinically after a change from a CREMOPHOR-EL based propofol formulation to the currently marketed soybean oil and lecithin based formulation; for example, see Mirakhur, R. K. (1988), Stark et al. (1985), Mangar and Holak (1992), White and Negus (1991), and Ghouri et al. (1994) herein.

Pain at the site of injection of propofol may be related to the concentration of propofol; for example, see Smith, I., White, P. F., Nathanson, M. and Gouldson, R. (1994) "Propofol—An update on its clinical use." Anesthesiology, 81, 1005–1043.

Compositions containing 1% and 2% propofol and a mixture of medium-chain triglycerides (MCT) and long-chain triglycerides (LCT) in a dispersed oil phase have produced lowered propofol concentrations in an aqueous phase; see for example Babl, J., Doenicke, A., and Monch, V. (1995) "New propofol LCT/MCT fat emulsions as solvent. Approach to reducing pain on injection of propofol," Eur. Hosp. Pharmacy, 1, 15–21 and Doenicke, A. W., Babl, J., Kellermann, W., Rau, J., and Roizen, M. F. (1996) "Reducing pain during propofol injection: the role of the solvent," Anesth. Analg., 82, 472–4.

While the use of medium chain triglycerides in a propofol formulation in human volunteers can lower the incidence of severe or moderate pain on injection relative to that seen after injection of a commercially available propofol formulation, significantly higher amounts of oil (up to 20% w/v MCT, LCT, and vegetable oil) were required to produce the result (see for example Doenicke, A. W., Babi, J., Klotz, U., Kugler, J., O'Connor, M., Rau, J., Roizen, M. F. (1997) "Pharmacokinetics and pharmacodynamics of propofol in a new solvent," Anesth. Analg., 85, 1399–403; Babl et al. (1995); and Doenicke et al. (1996 and 1997).

In an experimental rat model Cox et al. (1998) "Influence of different fat emulsion-based intravenous formulations on the pharmacokinetics and pharmacodynamics of propofol," Pharmaceutical Research, 15 (3), 442–448 found that the pharmacokinetics and pharmacodynamics of propofol are neither affected by the type of oil nor by the concentration of propofol in an intravenous formulation. While significantly increasing the amount of oil may aid in reducing pain on injection, oil levels as high as 20% are likely to further compromise patients undergoing prolonged administration of propofol, for example in intensive care units, and potentially lead to hyperlipidemia in those patients.

Haynes in U.S. Pat. No. 5,637,625 recognized two problems associated with the use of large quantities of vegetable oil in the commercial DIPRIVAN formulation: hyperlipidemia in patients undergoing long-term sedation in an intensive care unit (ICU), and the risk of bacterial contamination and growth in the high lipid content formulation that lacked antimicrobial preservatives. U.S. Pat. No. 5,637,625 disclosed formulations of phospholipid coated micromatrices or microdroplets of propofol devoid of fats and triglycerides that provided anesthesia and chronic sedation over extended periods of time without fat overload. Haynes' microdroplet formulations are bactericidal (e.g. self-sterilizing) in large part because they are free of material that will support bacterial growth. This gave the formulations an extended shelf life.

Three of the most often cited shortcomings of currently marketed or previously disclosed formulations are the potential for growth of microorganisms in the formulation, the induction of local irritation and/or pain at the site of injection, and the use of high levels of lipid.

BRIEF DESCRIPTION OF THE INVENTION

This invention discloses compositions of sterilized, injectable homogenized dispersions of micromatrices or microdroplets containing propofol suspended in an aqueous medium and containing an antimicrobial agent. The micromatrices or microdroplets have a mean diameter from about 50 nm to about 1000 nm and consist essentially of about 1% to about 7.5% of propofol, about 1% to about 8% of a propofol-soluble diluent, and about 0.67% to about 5% of a surface stabilizing amphiphilic agent with the proviso that the ratio of propofol to diluent is in the range of about 0.25 to about 7.5 while the ratio of propofol to amphiphilic agent is in the range from about 0.4 to about 1.5. The aqueous medium contains a pharmaceutically acceptable water-soluble hydroxyl-group-containing excipient in an amount sufficient to adjust the osmolality of the final sterilized dispersion to be isotonic with blood. The viscosity of a composition of this invention is in the range from about 1.1 to 8 cps, preferably in the range from about 4 to 6 cps.

In preferred embodiments, the dispersions contain a synergetic quantity of antimicrobial agent. In one aspect, a synergetic quantity of antimicrobial agent can be characterized as an amount of antimicrobial agent below the threshold of efficacy of the antimicrobial agent. Antimicrobial efficacy is an ability to retard or inhibit microbial growth.

In one embodiment, the threshold of efficacy of an antimicrobial agent can be defined as the minimum amount of the antimicrobial agent which permits no more than a 0.5 log increase in microbial growth over at least 7 days (168 hours) from the level of an initial inoculum of each of *Staphylococcus aureus* (ATCC 6538), *Escherichia coli* (ATCC 8739 and ATCC 8454), *Pseudomonas aeruginosa* (ATCC 9027), *Candida albicans* (ATCC 10231), and *Aspergillus niger* (ATCC 16403) added at approximately 1000 colony forming units (CFU) per milliliter to a reference dispersion at a temperature in the range 20–25° C. To identify a threshold of efficacy amount of an antimicrobial agent, a washed suspension of each organism is added to a separate aliquot of a homogenized reference dispersion of micromatrices or microdroplets consisting of a propofol-soluble diluent and an amphiphilic agent suspended in an aqueous medium containing a pharmaceutically acceptable water-soluble hydroxyl-group-containing excipient in an amount sufficient to adjust the osmolality of the reference dispersion to be isotonic with blood, the ratio of propofol-soluble diluent to amphiphilic agent being substantially that of the propofol-containing dispersions of this invention. The inoculated reference dispersion is incubated at 20–25° C. for up to 7 days, and viable colonies of the organism are counted at 24 hours after inoculation, at 48 hours after inoculation, and at 7 days or 168 hours after inoculation. A threshold of efficacy amount can be established by increasing or decreasing the concentration of antimicrobial agent to achieve no more than a 0.5 log increase as described above.

In another aspect the antimicrobial efficacy of an amount of antimicrobial agent at any concentration can be determined in a reference dispersion relative to its antimicrobial efficacy at higher and lower concentrations and relative to the same concentration in the presence and absence of propofol. If the antimicrobial activity of a dispersion of micromatrices or microdroplets of this invention containing propofol and an antimicrobial agent is greater than the sum of the antimicrobial activity of a reference dispersion of micromatrices or microdroplets containing propofol but without the antimicrobial agent plus the antimicrobial activity of a reference dispersion of micromatrices or microdroplets containing the antimicrobial agent but without propofol, then the antimicrobial activity of the dispersion of this invention is the result of a synergy among the components, and the amount of antimicrobial agent is a synergetic quantity. In this regard, a synergetic quantity thus can be an amount or concentration of antimicrobial agent above the threshold of efficacy amount in a composition of this invention.

The compositions of the invention are antimicrobial, inhibit or retard the growth of extrinsically added microbes such as bacteria and fungi, do not induce local irritation and/or pain at the site of injection, and do not contain high levels of lipid thereby substantially reducing the propensity of a patient to develop hyperlipidemia as a result of administration of propofol in the compositions relative to that of DIPRIVAN.

The compositions of this invention are useful for the production and maintenance of ambulatory anesthesia, neurosurgical anesthesia, neuroanesthesia and pediatric anesthesia; for monitored anesthesia care; for intensive care sedation; for general sedation, for cardiac anesthesia, for treatment of migraine headaches and cephalalgia, as antiemetics and the prevention of emesis, as well as other clinical uses.

Also disclosed are processes for the preparation of compositions of this invention. In one embodiment, a preferred process comprises, in the following sequence of steps, the formation of a lipophilic phase containing about 1% to about 7.5% propofol, about 1% to about 8% of a propofol-soluble diluent, and about 0.67% to about 5% of a surface stabilizing amphiphilic agent dissolved or dispersed therein with the proviso that in the dispersion the ratio of propofol to diluent is in the range of about 0.25 to about 7.5 while the ratio of propofol to amphiphilic agent is in the range from about 0.4 to about 1.5; the separate formation of an aqueous phase before, during, or after the formation of the lipophilic phase, which aqueous phase contains a pharmaceutically acceptable water-soluble hydroxyl-group-containing excipient in an amount sufficient to adjust the osmolality of the final dispersion to be isotonic with blood and a synergetic quantity of an antimicrobial agent; the mixing of the lipophilic phase and the aqueous phase to form a premix; the homogenization of the premix to form a dispersion of micromatrices or microdroplets containing propofol and a propofol-soluble diluent, the micromatrices or microdroplets stabilized by surface stabilizing amphiphilic agent and suspended in an aqueous medium containing a pharmaceutically acceptable water-soluble hydroxyl-group-containing excipient in an amount sufficient to adjust the osmolality of the final dispersion to be isotonic with blood, the dispersion also containing a synergetic quantity of antimicrobial agent; the dispensing of an aliquot of said dispersion into a vial followed by the sealing of said vial; and then terminal steam sterilization to form a sterilized final dispersion.

In another embodiment, the process comprises, in the following order, the formation of a lipophilic phase containing about 1% to about 7.5% propofol and about 1% to about 8% of a propofol-soluble diluent; the separate formation before, during, or after the formation of the lipophilic phase of an aqueous phase containing a pharmaceutically acceptable water-soluble hydroxyl-group-containing excipient in an amount sufficient to adjust the osmolality of the final dispersion to be isotonic with blood, a synergetic quantity of an antimicrobial agent, and about 0.67% to about 5% of a surface stabilizing amphiphilic agent dissolved or dispersed therein with the proviso that the ratio of propofol to diluent is in the range of about 0.25 to about 7.5 while the ratio of propofol to amphiphilic agent is in the range from about 0.4 to about 1.5 in the final dispersion; the mixing of the lipophilic phase and the aqueous phase to form a premix; the homogenization of the premix to form a dispersion of micromatrices or microdroplets containing propofol and a propofol-soluble diluent stabilized by the surface stabilizing amphiphilic agent suspended in an aqueous medium containing a pharmaceutically acceptable water-soluble hydroxyl-group-containing excipient in an amount sufficient to adjust the osmolality of the dispersion to be isotonic with blood, the dispersion containing a synergetic quantity of antimicrobial agent; the dispensing of an aliquot of said dispersion into a vial followed by the sealing of said vial; and a terminal steam sterilization step to form a sterile final dispersion.

The vials can be cooled to ambient temperature after thermal sterilization by a number of means including cooling by immersion in a bath of cooling water e.g., a bath maintained at ambient or other temperature below the sterilization temperature, or a bath of cooling water maintained with a temperature gradient such as −1° C. per minute to control the rate of cooling of the vials that were heated during sterilization. Alternatively, the vials may be cooled in ambient air such as in a sterile environment in a GMP approved manufacturing facility.

An aliquot of the dispersion can be from about 1 milliliter to about 1 liter or 2 liters, preferably from about 1 milliliter to about 500 milliliters, more preferably from about 5 milliliters to about 250 milliliters, and most preferably from about 10 milliliters to about 100 milliliters. A vial is preferably about 10 to 25% larger than the aliquot to be dispensed therein. Preferably, the process of preparing a dispersion of this invention is carried out in an inert, non-oxidizing atmosphere such as in a nitrogen or argon atmosphere. Preferably, the vials contain no oxygen, and the dispensing of the aliquots and sealing operations are done in an atmosphere of an inert gas such as nitrogen or argon. It is preferred that the amount of the dispersion of this invention in a sealed vial be slightly larger than the total amount of the dispersion to be withdrawn from the vial during expected or anticipated clinical use. By slightly larger we mean about 1 to 5% larger, preferably 1% to about 3% larger than the expected amount to be used. This allows the removal of a dose or repeated removal of doses required to achieve a clinically effective result while leaving a slight excess of the dispersion available to allow for dead volumes in a needle, syringe or giving set or similar device, and minimizes waste of amounts approximating a required effective amount or dose.

In one embodiment of a process of this invention, an antimicrobial agent can be added to the aqueous phase prior to the formation of the premix.

In another embodiment of a process of this invention, an antimicrobial agent can be added to the premix prior to homogenization of the premix and formation of the dispersion of micromatrices or microdroplets.

In another embodiment of a process of this invention, an antimicrobial agent can be added after homogenization of the premix and formation of the dispersion of micromatrices or microdroplets but prior to the aliquoting of the dispersion into vials.

In another embodiment of a process of this invention, an antimicrobial agent can be added to a vial, optionally in pure form or in the form of an aqueous solution or in the form of a suspension compatible with the dispersion of micromatrices or microdroplets containing propofol, which dispersion is then added to the vial.

A solution or suspension containing the antimicrobial agent and compatible with the dispersion may also contain one or more pharmaceutically acceptable water-soluble hydroxyl-group-containing excipient, preferably the excipient that is used in the dispersion.

A solution or suspension containing the antimicrobial agent and compatible with the dispersion may contain one or more pharmaceutically acceptable surface stabilizing amphiphilic agent, preferably the surface stabilizing amphiphilic agent used in the dispersion.

A suspension containing the antimicrobial agent and compatible with the dispersion may contain one or more propofol-soluble diluent together with one or more pharmaceutically acceptable surface stabilizing amphiphilic agent in the form of a suspension of micromatrices or microdroplets of propofol-soluble diluent stabilized with one or more pharmaceutically acceptable surface stabilizing amphiphilic agent. Preferably, the diluent is the same as that used in the dispersion or preferably the amphiphilic agent is the same as that used in the dispersion. More preferably, both the diluent and the amphiphilic agent are the same as those used in the dispersion.

A suspension compatible with the dispersion may contain a more concentrated dispersion of the propofol-containing micromatrices or microdroplets of this invention, i.e., it can have less water. The process of mixing two compatible dispersions, one of which is a concentrated dispersion and one of which is a diluting dispersion, results in a dilution of the more concentrated dispersion. Preferably the ratio of propofol to diluent and the ratio of propofol to amphiphilic agent of the concentrated and diluting dispersion are the same in each dispersion. The dispersions are thus substantially similar except for the amount of water in each, the concentrated dispersion having less water and the diluting dispersion having more water, and except for the presence of antimicrobial agent in the concentrated dispersion.

In another embodiment of this invention, a first dilute dispersion not containing an antimicrobial agent and a second concentrated dispersion containing an antimicrobial agent are prepared and are then mixed together. In this embodiment, a first dilute dispersion can contain micromatrices or microdroplets of propofol and a propofol-soluble diluent and be stabilized with an amphiphilic agent. The first dispersion can be prepared by homogenizing the components in an aqueous medium containing a pharmaceutically acceptable water-soluble hydroxyl-group-containing excipient. Homogenization can be by a process using high sheer such as high-pressure homogenization, microfluidization, sonication, and the like. A second, concentrated dispersion containing micromatrices or microdroplets of propofol and a propofol-soluble diluent and stabilized with an amphiphilic agent can be prepared by homogenizing the components in an aqueous medium optionally containing a pharmaceutically acceptable water-soluble hydroxyl-group-containing excipient and an antimicrobial agent where the amount of water in the first, diluted dispersion is less than the amount of water in the second dispersion. The amount of water in the second dispersion can be from about 10% to about 95% of the amount of water in the first dispersion. A portion of the first dispersion can be mixed with an aliquot of the second dispersion to achieve a composition of this invention that can be sterilized to achieve a final dispersion. The mixing of the dispersions can be done in bulk prior to dispensing into vials followed by sealing of the vials and sterilization or it can be done in individual vials prior to sterilization. The ratio of the amounts of first dispersion and second dispersion and the amount of pharmaceutically acceptable water-soluble hydroxyl-group-containing excipient in each can be selected to achieve a composition having ratios and concentrations according to this invention.

Percentages of ingredients used in the description of this invention are meant to be the percentages of the ingredients in the final dispersion. Actual amounts and relative amounts used can be readily calculated by one skilled in the art.

In another embodiment of a process of this invention, a first dispersion of micromatrices or microdroplets containing propofol can be prepared according to this invention but made to contain a concentrated amount of antimicrobial agent. This first dispersion can be added to a second dispersion of propofol micromatrices or microdroplets containing a propofol-soluble diluent and stabilized by a surface stabilizing amphiphilic agent prepared in a manner similar to or according to this invention but without the addition of an antimicrobial agent, or prepared by a method otherwise known in the art without the addition of an antimicrobial agent, to provide a final composition according to this invention containing an amount of antimicrobial agent wherein the diluted amount is a synergetic quantity of antimicrobial agent. The concentrated amount of antimicrobial agent can be for example a 2 fold amount to a 100 fold amount relative to a desired synergetic amount, and the dilution can be from about 100 fold to about 2 fold to achieve the desired synergetic amount or concentration in the final dispersion.

Additional process can be envisioned to prepare compositions of this invention that involve variations of the concentration of the dispersion, the amount of water, and the individual ingredients as well as the order of mixing of the ingredients. Such variations are anticipated by this invention.

Also disclosed in this invention are methods of treatment or methods of use of compositions of this invention. Thus, disclosed are a method for the production and maintenance of ambulatory anesthesia in a patient; a method for the production and maintenance of neurosurgical anesthesia in a patient; a method for the production and maintenance of anesthesia in a pediatric patient; a method for the production and maintenance of anesthesia in monitored care of a patient; a method for the production and maintenance of sedation of a patient in intensive care; a method for the production and maintenance of general sedation in a patient; a method of treatment and alleviation of a migraine headache in a patient; and a method of treatment and alleviation of emesis in a patient. The patient can be a human or an animal, and the method can optionally be practiced in a hospital setting for a human patient and a veterinary clinic or hospital for an animal. Animals include domestic animals such as a dog, cat, horse, cow, sheep, pig, and wild animals such as those kept in zoos such as lions, tigers, bears, monkeys, apes and the like.

A method of use or a method of treatment of a patient with compositions of this invention comprises administering to a patient by intravenous injection a composition of a sterilized, injectable homogenized dispersion of micromatrices or microdroplets containing propofol suspended in an aqueous medium, the micromatrices or microdroplets having a mean diameter from about 50 nm to about 1000 nm and consisting essentially of about 1% to about 7.5% of propofol, about 1% to about 8% of a propofol-soluble diluent, and about 0.67% to about 5% of a surface stabilizing amphiphilic agent with the proviso that the ratio of propofol to diluent is in the range of about 0.25 to about 7.5 while the ratio of propofol to amphiphilic agent is in the range from about 0.4 to about 1.5, the aqueous medium containing a pharmaceutically acceptable water-soluble hydroxyl-group-containing excipient in an amount sufficient to adjust the osmolality of the dispersion to be isotonic with blood, the viscosity of the dispersion being in the range from about 1.1 to 8 cps, the dispersion also containing a synergetic quantity of antimicrobial agent, which homogenized dispersion does not induce irritation or pain at the site of injection and does not enhance induce hyperlipidemia in the patient.

A method of treatment can comprise the injection into a patient of a composition of this invention. The injection can be in a bolus form or it can be administered by infusion in an aqueous liquid, preferably an aqueous liquid isotonic with blood, such as in an aqueous solution of a nutrient or electrolyte or phosphate buffered saline or other liquid infused during treatment of a patient such as before, and/or during, and/or after a surgical procedure; or as part of a life maintenance procedure; or during and/or after a hydration procedure; or as part of a treatment with an intravenously administered nutrition supplement. The injection can be made contiguous with an invasive surgical procedure, cancer surgery, dental surgery, treatment of a patient with a burn, treatment of a patient suffering from the effect of a crush injury, treatment of a patient suffering from the effect of an automobile accident or an accidental fall, treatment of patients undergoing cosmetic or restorative surgery, and other surgical procedures. Optionally, the aqueous dispersion can be mixed with or can contain other drugs such as other anesthetic agents such as lidocaine.

In another embodiment, a method of use of this invention comprises administering to a patient by intravenous injection a composition of a sterilized, injectable homogenized dispersion of micromatrices or microdroplets containing propofol suspended in an aqueous medium, the micromatrices or microdroplets having a mean diameter from about 50 nm to about 1000 nm and consisting essentially of about 1% to about 7.5% of propofol, about 1% to about 8% of a propofol-soluble diluent, and about 0.67% to about 5% of a surface stabilizing amphiphilic agent with the proviso that the ratio of propofol to diluent is in the range of about 0.25 to about 7.5 while the ratio of propofol to amphiphilic agent is in the range from about 0.4 to about 1.5, the aqueous medium containing a pharmaceutically acceptable water-soluble hydroxyl-group-containing excipient in an amount sufficient to adjust the osmolality of the dispersion to be isotonic with blood, the viscosity of the dispersion being in the range from about 1.1 to 8 cps, the dispersion also containing a synergetic quantity of antimicrobial agent, which dispersion does not induce irritation or pain at the site of injection and does not enhance or induce hyperlipidemia in the patient wherein the composition is withdrawn by a syringe with a needle from a sealed vial by puncturing a seal on the vial containing the composition, the contents of the syringe then being administered to the patient.

In another embodiment, a method of use of this invention comprises administering to a patient by intravenous injection a composition of a sterilized, injectable homogenized dispersion of micromatrices or microdroplets containing propofol suspended in an aqueous medium, the micromatrices or microdroplets having a mean diameter from about 50 nm to about 1000 nm and consisting essentially of about 1% to about 7.5% of propofol, about 1% to about 8% of a propofol-soluble diluent, and about 0.67% to about 5% of a surface stabilizing amphiphilic agent with the proviso that the ratio of propofol to diluent is in the range of about 0.25 to about 7.5 while the ratio of propofol to amphiphilic agent is in the range from about 0.4 to about 1.5, the aqueous medium containing a pharmaceutically acceptable water-soluble hydroxyl-group-containing excipient in an amount sufficient to adjust the osmolality of the dispersion to be isotonic with blood, the viscosity of the dispersion being in the range from about 1.1 to 8 cps, the dispersion also containing a synergetic quantity of antimicrobial agent, which dispersion does not induce irritation or pain at the site of injection and does not enhance or induce hyperlipidemia in the patient wherein the composition is withdrawn by a syringe with a needle from a sealed vial by puncturing a seal on the vial containing the composition, the contents of the syringe then being administered to the patient, wherein seal on the vial has been previously punctured by a syringe needle.

In another method of use of this invention, a first aliquot or dose of a dispersion of this invention is removed from a sealed vial by means of a first needle such as a syringe needle that punctures the seal on the vial, and the first aliquot or dose is then administered intravenously to a patient. Subsequently, a second aliquot or dose of the dispersion in the vial is removed by means of a second needle puncturing the previously punctured seal on the vial, and the second aliquot or dose is administered to a patient which can be the same patient that received the first aliquot or a second patient. The two doses can be the same amount of dispersion or different amounts, preferably anesthetically effective amounts or sedatively effective amounts. The process of puncturing the seal on the vial with a needle and removing an aliquot or dose of dispersion can be repeated until substantially all of the useful doses of the dispersion in the vial are withdrawn. The time period can be up to 168 hours during which the process of puncturing the seal on the vial and removing aliquots or doses of dispersion in the vial can be repeated after the initial puncture of the seal, preferably the time period can be up to 48 hours, and most preferably up to 24 hours.

It is an advantage that portions or aliquots or doses (including equal or unequal doses) of the contents of a vial containing a composition of this invention can be separately removed from the vial by separate punctures of the seal on the vial by a method employing a needle for each puncture. The compositions of this invention prevent or inhibit growth of extrinsically added microbes such as bacteria and fungi that may be introduced or inoculated into the composition as a result of repeated puncturing of the seal on the vial. The antimicrobial activity of the composition derives from a synergetic combination of antimicrobial activity of the antimicrobial agent and the antimicrobial activity of the propofol dispersion inherent in the composition in the absence of the antimicrobial agent.

In one aspect of this invention, the combination of antimicrobial activity of the antimicrobial agent and the antimicrobial activity of the propofol dispersion inherent in the composition in the absence of the antimicrobial agent is additive, particularly when the concentration of antimicrobial agent is below the threshold of efficacy described herein. In a preferred aspect, the combination of antimicrobial activity of the antimicrobial agent and the antimicrobial activity of the propofol composition inherent in the composition in the absence of the antimicrobial agent is synergetic, with the total antimicrobial activity being greater than the sum of the antimicrobial activity of the antimicrobial agent and the antimicrobial activity of the propofol composition inherent in the composition in the absence of the antimicrobial agent.

In another aspect the invention comprises a method for synergetically increasing the antimicrobial activity of a composition of a sterilized, injectable homogenized dispersion of micromatrices or microdroplets containing propofol suspended in an aqueous medium, the micromatrices or microdroplets having a mean diameter from about 50 nm to about 1000 nm and consisting essentially of about 1% to about 7.5% of propofol, about 1% to about 8% of a propofol-soluble diluent, and about 0.67% to about 5% of a surface stabilizing amphiphilic agent with the proviso that the ratio of propofol to diluent is in the range of about 0.25 to about 7.5 while the ratio of propofol to amphiphilic agent is in the range from about 0.4 to about 1.5, the aqueous medium containing a pharmaceutically acceptable water-soluble hydroxyl-group-containing excipient in an amount sufficient to adjust the osmolality of the dispersion to be isotonic with blood, the viscosity of the dispersion being in the range from about 1.1 to 8 cps, the method comprising the addition to the dispersion of a synergetic quantity of antimicrobial agent, which dispersion does not induce irritation or pain at the site of injection and does not enhance induce hyperlipidemia in the patient.

In one aspect, this invention provides a method of synergetically increasing the antimicrobial efficacy against microbial growth in a stable, sterilized, substantially non-irritating, injectable, homogenized dispersion of micromatrices or microdroplets containing propofol suspended in an aqueous medium containing a pharmaceutically acceptable water-soluble hydroxyl-group-containing excipient in an amount sufficient to adjust the osmolality of the dispersion to be isotonic with blood, by incorporating a synergetic quantity of a water-soluble or partially water-soluble antimicrobial agent into the dispersion, wherein said micromatrices or microdroplets have a mean diameter from about 50 nm to about 1000 nm and are comprised of about 1% to about 7.5% of propofol, about 1% to about 8% of a propofol-soluble diluent, and about 0.67% to about 5% of a surface stabilizing amphiphilic agent in which the ratio of propofol to diluent is in the range of about 0.25 to about 7.5 while the ratio of propofol to amphiphilic agent is in the range from about 0.4 to about 1.5, and wherein the viscosity of the dispersion is in the range of 1.1 to 8 cps.

In another aspect, this invention provides a method of synergetically increasing the antimicrobial efficacy against microbial growth in a vial or giving set in contact with a stable, sterilized, substantially non-irritating, injectable, homogenized dispersion of micromatrices or microdroplets of propofol suspended in an aqueous medium containing a pharmaceutically acceptable water-soluble hydroxyl-group-containing excipient in an amount sufficient to adjust the osmolality of the dispersion to be isotonic with blood, by incorporating a synergetic quantity of a water-soluble or partially water-soluble antimicrobial agent into the dispersion, wherein said micromatrices or microdroplets have a mean diameter from about 50 nm to about 1000 nm and are comprised of about 1% to about 7.5% of propofol, about 1% to about 8% of a propofol-soluble diluent, and about 0.67% to about 5% of a surface stabilizing amphiphilic agent in which the ratio of propofol to diluent is in the range of about 0.25 to about 7.5 while the ratio of propofol to amphiphilic agent is in the range from about 0.4 to about 1.5, and wherein the viscosity of the dispersion is in the range of 1.1 to 8 cps. In this aspect the vial can be sealed and steam sterilized, and then the seal of the vial can be punctured by a needle at least once such as by a syringe needle used to withdraw an aliquot or dose of the dispersion from the vial or to allow the contents of the vial to be removed in whole or in part. The seal of the vial can be punctured by a needle at least twice (i.e., two or more times) such as by a syringe needle used to repeatedly withdraw aliquots or doses of the dispersion from the vial.

The antimicrobial agent useful in this invention can be a single agent or a combination of one or more antimicrobial agents. The antimicrobial agent can be water-soluble or partially water-soluble. The antimicrobial agent can be completely dissolved in the aqueous medium of a composition of this invention or can be partly dissolved in the aqueous medium of a composition of this invention. In one embodiment, if the antimicrobial agent is partly dissolved in the aqueous medium, a portion of the antimicrobial agent that is not dissolved in the aqueous medium can reside in the micromatrices or microdroplets containing propofol or in micromatrices or microdroplets containing a propofol-soluble diluent. In another embodiment, the antimicrobial agent can reside is structures stabilized by a surface stabilizing amphiphilic agent such as in one or more bilayer structures and structures containing amphiphilic agent such as those described in U.S. Pat. No. 5,091,188.

The micromatrices or microdroplets containing propofol of this invention have a mean diameter from about 50 nm to about 1000 nm, preferably from about 50 nm to about 800 nm, and consist essentially of about 1% to about 7.5% of propofol, about 1% to about 8% of a propofol-soluble diluent, and about 0.67% to about 5% of a surface stabilizing amphiphilic agent with the proviso that the ratio of propofol to diluent is in the range of about 0.25 to about 7.5 while the ratio of propofol to amphiphilic agent is in the range from about 0.4 to about 1.5.

Surprisingly, in this invention certain propofol compositions each prepared as an injectable aqueous dispersion of a water-insoluble micromatrix or dispersion consisting of propofol and one or more propofol-soluble agents or diluents and one or more antimicrobial agents present in a synergetic quantity in the dispersion are capable of substantially limiting or inhibiting the growth of certain microorganisms to a substantially greater degree or extent than is otherwise expected from the antimicrobial property or antimicrobial activity of the propofol formulation alone or from the antimicrobial activity of the antimicrobial agent alone in the concentrations defined herein. Furthermore, it is surprising that the compositions of this invention containing a combination of a dispersion containing propofol plus antimicrobial agent do not display evidence of local irritation at the injection site.

DETAILED DESCRIPTION OF THE INVENTION

This invention provides a sterilized, injectable homogenized dispersion of micromatrices or microdroplets containing propofol suspended in an aqueous medium and containing a synergetic quantity of antimicrobial agent, wherein the micromatrices or microdroplets have a mean diameter from about 50 nm to about 1000 nm and consist essentially of about 1% to about 7.5% of propofol, about 1% to about 8% of a propofol-soluble diluent, and about 0.67% to about 5% of a surface stabilizing amphiphilic agent with the proviso that the ratio of propofol to diluent is in the range of about 0.25 to about 7.5 while the ratio of propofol to amphiphilic agent is in the range from about 0.4 to about 1.5; and wherein the aqueous medium contains a pharmaceutically acceptable water-soluble hydroxyl-group-containing excipient in an amount sufficient to adjust the osmolality of the final sterilized dispersion to be isotonic with blood; and wherein the viscosity of a composition of this invention is in the range from about 1.1 to 8 cps, preferably in the range from about 4 to 6 cps.

The compositions of this invention have a low lipid content, do not support microbial growth according to guidelines comprising a US Pharmacopoeia preservative effectiveness test, do not cause discernable local irritation around a site of injection in an patient, provide substantially reduced levels of pain on injection relative to currently available compositions containing propofol, can be terminally steam sterilized, and are stable as microemulsions in the presence of the antimicrobial agent for at least six months, more preferably at least one year, even more preferably for at least 18 months, and most preferably for at least two years. The compositions are useful in anesthetic and sedative applications in mammals.

The novel compositions described in this invention consist of dispersions of nanometer to micrometer size water-insoluble micromatrices or microdroplets comprising from 1% to about 7.5% propofol dispersed in an injectable aqueous phase.

The water-insoluble micromatrices or water-insoluble microdroplets of a dispersion of this invention comprise one or more lipophilic agents or propofol-soluble diluents. The diluents can be dissolved in the propofol as a liquid or as a solid or as a slush, i.e., as a mixture of liquid and solid. The dispersion exhibits a level of antimicrobial activity related to the ratio of ingredients in the dispersion.

A dispersion of this invention does not give rise to substantial irritation to tissue on intravenous injection in a patient. In one embodiment, a dispersion of this invention does not cause local reaction or irritation at the site of injection in an animal.

When the composition in the micromatrix is completely liquefied, each micromatrix particle is a microdroplet. At temperatures where the composition inside the micromatrix can be a solid or a semisolid such as in the form of a solid solution inside the micromatrix particles that are suspended in liquid water, or a composition that is a semisolid solution of propofol in a propofol-soluble diluent in an aqueous suspension, or a frozen suspension of microdroplets (the melting point of propofol being about 19° C.), the liquid in the microdroplets can become solidified or partially solidified in the form of a slush with solid and liquid forms of the mixture of propofol and propofol-soluble diluent being in equilibrium.

In one embodiment, the propofol-soluble diluent can dissolve in propofol at all temperatures. In another embodiment, the propofol-soluble diluent can dissolve in propofol at an elevated temperature such at a temperature between about 40° C. to about the boiling point of water, preferably between 40° C. to about 80° C., and can partially separate from propofol in a micromatrix particle on cooling to about 30° C. or lower. In this case the solubility in propofol is dependent on temperature. In another embodiment, the propofol and propofol-soluble diluent can form a solid solution in the micromatrix. In another embodiment, the propofol and propofol soluble diluent can form a solid solution in the micromatrix below about 37° C., preferably below about 32° C. and form a liquid solution at about 37° C., preferably above 32° C. In this aspect of the invention, the presence of propofol in a solidified or partially solidified micromatrix reduces the immediate bioavailability of the drug at the site of injection of a suspended dispersion of the micromatrix and substantially reduces or eliminates pain and/or irritation of tissues at the site of injection with respect to the levels of pain and irritation associated with a formulation of DIPRIVAN. By a low melting solid solution in a micromatrix or a low melting solidified micromatrix solution we mean a micromatrix having a solid solution core that melts and becomes a liquid solution below the body temperature of a patient. When a suspended dispersion of a low melting solidified micromatrix solution or a low melting semisolid micromatrix solution enters the body of a patient at a site of injection, it mixes with the blood and is carried away from the site of injection while it rapidly melts and becomes a dispersion of microdroplets containing propofol with intended efficacy in the uses outlined herein (e.g., as an anesthetic agent or a sedative agent, or other uses). As a solid but low melting solution, a low concentration of propofol as a liquid at the site of injection can contribute to a reduction in irritation at the site of injection relative to a completely liquid propofol solution or relative to DIPRIVAN.

Propofol is 2,6-diisopropyl phenol, has a reported melting point of 18° C. (Aldrich Chemical Co.) to 19° C. (Merck Index), a boiling point of 256° C. at 760 mm, and a density of 0.955 g/mL at 20° C. Propofol is available from Albemarle Corporation, Baton Rouge, La., US.

Examples of useful lipophilic agents (or useful propofol-soluble diluents) include but are not limited to C-2 to C-24 saturated fatty acid C-2 to C-24 alcohol esters or C-8 to C-24 unsaturated fatty acid C-2 to C-24 alcohol esters acceptable for injection such as isopropyl myristate, isopropyl palmitate, cholesteryl oleate, ethyl oleate, palmitoyl acetate; saturated or unsaturated naturally available and pharmaceutically acceptable hydrocarbons having from 15 to 35 carbon atoms including squalene and squalane and analogous pharmaceutically acceptable hydrocarbon alcohols such as cholesterol, pharmaceutically acceptable terpenoid hydrocarbons and hydroxyl-substituted terpenoids having from 15 to 35 carbons atoms, alpha-tocopherol and hydrogenated derivatives of alpha-tocopherol, cannabinoids such as THC, pharmaceutically acceptable aralkyl hydrocarbons and hydroxyl-substituted aralkyl hydrocarbons having from 15 to 35 carbons, aliphatic C-8 to C-20 esters and triglycerides of medium chain (C-8 to C-12) saturated and unsaturated pharmaceutically acceptable fatty acids of synthetic or natural origin, and aliphatic C-8 to C-14 esters and triglycerides of long chain (C-14 to C-30) saturated and unsaturated pharmaceutically acceptable fatty acids of synthetic or natural origin such as eicosapentaenoic acid and docosahexaenoic acid. Natural triglycerides can be selected particularly from vegetable and animal sources, e.g., pharmaceutically acceptable vegetable oils such as soy oil, safflower oil, cottonseed oil, corn oil, sunflower oil, arachis oil, castor oil, olive oil, and coconut oil, and pharmaceutically acceptable fish oils some of which are also known as omega-3 polyunsaturated oils, and omega-3 marine triglycerides. The oils can be single oils or mixtures of two or more oils.

More specifically, the diluent is preferably selected from the group consisting of a C-2 to C-24 saturated fatty acid C-2 to C-24 alcohol ester, a C-8 to C-24 unsaturated fatty acid C-2 to C-24 alcohol ester, saturated and unsaturated naturally available and pharmaceutically acceptable hydrocarbons and hydrocarbon alcohols having from 15 to 35 carbon atoms, triglycerides of medium chain C-8 to C-12 saturated and unsaturated pharmaceutically acceptable fatty acids, triglycerides of long chain C-14 to C-30 saturated and unsaturated pharmaceutically acceptable fatty acids, a pharmaceutically acceptable oil from a vegetable or fish, and mixtures thereof.

In preferred embodiments, the diluent is selected from the group consisting of isopropyl myristate, isopropyl palmitate, cholesteryl oleate, ethyl oleate, palmitoyl acetate, squalene, squalane, MIGLYOL-810™, capric-caprylic triglyceride, soybean oil, and mixtures thereof.

Selection of an oil or a mixture of oils known to be safe and rapidly cleared from the body after intravenous injection can provide an increase in metabolic clearance rate of an antimicrobial agent when used as an additive in this invention. In this invention a preferred oil is a combination or mixture of a LCT and a MCT, preferably a 1:1 mixture of a LCT and a MCT, for example preferably a 1:1 mixture of soybean oil which is an LCT and capric-caprylic triglyceride (MICLYOL-810) which is an MCT. Examples of preferred propofol-soluble diluents include ethyl oleate, NF available from Croda Leek Ltd., Staffordshire, UK, soybean oil, USP available from Spectrum, New Brunswick, N.J., US, and MIGLYOL-810 available from Hüls America, Piscatway, N.J., US.

At the surface of the water-insoluble micromatrices or microdroplets or otherwise at the micromatrix-water interface or microdroplet-water interface is surface stabilizing amphiphilic agent or a mixture of surface stabilizing amphiphilic agents that stabilize the micromatrix or microdroplet dispersion against coalescence and against microemulsion collapse. In one embodiment of this invention, a surface stabilizing amphiphilic agent or a combination of surface stabilizing amphiphilic agents can lower and thus control the degree of local tissue reaction on injection by lowering the level of irritation caused by the dispersion on injection.

Examples of useful and preferred amphiphilic agents are selected from the group consisting of pharmaceutically acceptable phospholipids, pharmaceutically acceptable lecithins, and mixtures thereof. This includes for example one or more pharmaceutically acceptable charged or uncharged phospholipids of natural sources, e.g., egg or soy lecithin, hydrogenated lecithin, e.g., PHOSPHOLIPON-90H™ or PHOSPHOLIPON-100H™ from Nattermann, synthetic phospholipids such as phosphatidylcholines or phosphatidylglycerols, and other phospholipids such as those available from Avanti Polar Lipids. Additional examples of preferred surface stabilizing amphiphilic agents include 1,2-dimyristoyl-sn-glycero-3-phosphocholine (DMPC) and 1,2-dimyristoyl-sn-glycero-3-[phospho-rac-(1-glycerol)] (DMPG) which are available from Avanti Polar Lipids Inc., Alabaster, Ala., USA, LIPOID E80™ (egg lecithin), LIPOID EPC™ (egg phosphatidylcholine), LIPOID SPC™ (soy phosphatidylcholine), and LIPOID SPC-3™ (saturated soy phosphatidylcholine) which are available from Lipoid GmBH, Ludwigshafen as well as such phospholipid materials as L-alpha-phosphatidylcholine, palmitoyl-linoleoyl phosphatidylcholine, stearoyl-linoleoyl phosphatidylcholine, lysolecithin, phosphatidic acid, phosphatidyl-DL-glycerol, phosphatidylethanolamine, palmitoyl-oleoyl phosphatidylcholine, phosphatidylinositol, phosphatidylserine (and its sodium salt), 1,3-bis(sn-3-phosphatidyl)-sn-glycerol, 1,3-di(3-sn-phosphatidyl)-sn-glycerol and their sodium or disodium salts, and the hydrogenated phospholipid analogues of the unsaturated phospholipid materials. Mixtures of phospholipids and lecithins are useful.

In one embodiment, a surface stabilizing amphiphilic agent can further comprise a surfactant selected from the group consisting of a pharmaceutically acceptable non-ionic surfactant, a pharmaceutically acceptable ionic surfactant, and mixtures thereof. Thus, also useful are in this invention as surface stabilizing agents for micromatrices or microdroplets are combinations of one or more amphiphilic agent with one or more pharmaceutically acceptable non-ionic surfactant such as members of the poloxamer and the pluronic series of surfactants such as F68 and F108, poloxamines such as the tetronic series of surfactants, polyoxyethylene sorbitan esters, e.g., the TWEEN® series of surfactants, cholesterol in a combination with an amphiphilic agent, and combinations of one or more amphiphilic agent with one or more pharmaceutically acceptable ionic surface active agent such as bile acid salts and bile acid conjugates, as well as other pharmaceutically acceptable surface modifiers useful in pharmaceutical products suitable for injection.

The aqueous phase consists of water or water for injection buffered to a pH between about 5 to about 9, preferably from about pH 6 to about pH 8 by a pharmaceutically acceptable buffer salt such as phosphate buffer. The aqueous phase also comprises one or more pharmaceutically acceptable hydroxyl-group containing tonicity modifier such as one or more monosaccharide, disaccharide, trisaccharide, such as sucrose, dextrose, trehalose, mannitol, lactose, glycerol, glycerin, and the like such as sorbitol in a quantity sufficient to render the final composition isotonic with blood and thus suitable for intravenous injection. The milliosmolality of blood normally is in the range from about 250 to about 350 mOs/kg and averages about 300 mOs/kg. When the amount of hydroxyl-group containing tonicity modifier or combination of modifiers which can be polyhydroxy compounds in the formulation is selected such that the milliosmolality is not isotonic with blood and is greater than the tonicity of blood, the aqueous dispersion of this invention is a concentrate that can be diluted with or diluted by adding the concentrate into a suitable diluent such as water for injection or phosphate buffered water for injection or water containing other ingredients suitable for injection and useful in a surgical procedure or an isotonic sugar solution or an isotonic saline solution, especially prior to injection of the solution into tubing containing the solution in an iv drip or into a bulk container of the diluting solution to adjust the tonicity to the range of that of blood. Examples of preferred hydroxyl-group-containing excipients include Glycerin, USP-FCC and Mannitol, USP available from J. T. Baker, Philipsburg, N.J., US and (D+) Alpha, alpha-Trehalose available from Pfanstiehl Laboratories Inc, Waukegan, Ill., US. In one aspect of this invention, preferred compositions of this invention can contain mannitol or trehalose and have a viscosity greater than 1.1 cps, and preferably greater than 1.2 cps to about 5 cps. In other aspects of this invention, preferred compositions can have a viscosity as high as from about 1.2 cps to about 5.3 cps. It is postulated that such high viscosity compositions can exhibit reduced hemolytic potential on injection.

In a preferred embodiment the hydroxyl-group-containing excipient is selected from the group consisting of a monosaccharide, a disaccharide, a trisaccharide, sucrose, dextrose, trehalose, mannitol, lactose, glycerol, glycerin, sorbitol, and mixtures thereof.

Useful levels of glycerin are about 2.5% (w/w). Useful levels of mannitol are about 5.5% (w/w) to about 7.5% (w/w). Useful levels of trehalose are about 12% to about 20% (w/w). Preferred hydroxyl-containing tonicity modifiers are mannitol and trehalose. In these percentages, (w/w) implies weight of the ingredient per total weight of the formulation. A useful level or percentage of a hydroxyl-containing excipient or mixture of excipients is a tonicity-modifying amount.

In one embodiment, the aqueous phase may additionally contain an amount of a pH adjusting agent such as sodium hydroxide and/or a pharmaceutically acceptable acid such as HCl, the amount of which does not cause the pH of the compositions of this invention to be out of the range of 5 to 8 pH units, and the amount of which does not cause the emulsion to collapse.

In a preferred embodiment of this invention, antimicrobial agents present in the dispersion are water-soluble or partially water-soluble. In a synergetic quantity, an antimicrobial agent can be active at levels that normally would not provide protection against microbial growth in the absence of propofol and the other ingredients in the concentration ranges specified in this invention. There is a synergetic effect of such agents in the presence of the dispersions of this invention such that when a synergetic quantity is added to a dispersion composition described herein it confers antimicrobial stability to the dispersions in an amount greater than the dispersions alone provide and in an amount greater than the antimicrobial agent can provide at the concentration used. This can be measured by a USP Preservative Effectiveness Test. Preferred antimicrobial agents include those that do not have a high partition coefficient for the water-insoluble micromatrix or microdroplets of propofol and diluent, for example, EDTA, benzylalkonium chloride, benzethonium chloride, sodium benzoate, and sodium metabisulfite.

Certain antimicrobial compositions containing propofol are described in WO 00/10531. Each of these are prepared as an injectable aqueous dispersion of a water-insoluble micromatrix or microdroplet consisting of propofol and one or more propofol-soluble agents stabilized with a surface active agent that is preferably an amphiphilic agent such as a phospholipid or lecithin. The compositions described in WO 00/10531 are capable of substantially limiting or inhibiting the growth of certain microorganisms and do not cause local irritation at the injection site as evidenced by in-vivo experiments employing rat caudal veins. That invention did not require the addition of any antimicrobial preservative agents and the propofol compositions described in WO 00/10531 are effective at inhibiting the growth of low levels of microorganisms. However, the formulations of that invention having acceptably low levels of lipid content and displaying lack of vein irritation may not pass a USP Preservative Effectiveness Test that involves testing at higher levels of microorganisms. When certain compositions disclosed in WO 00/10531 and having the levels of propofol, diluent, and amphiphilic agent according to this invention are augmented by addition of a synergetic quantity of antimicrobial agent, the resulting formulations can pass a USP Preservative Effectiveness Test that involves testing at higher levels of microorganisms.

As a result, it is an advantage that the formulations of the present invention do not contain excessive amounts of one or more oil or triglyceride. It is an further advantage that the formulations of this invention substantially reduce the propensity of a patient to experience hyperlipidemia as a result of high lipid levels which are absent in the compositions of this invention.

It is another advantage that the formulations of the present invention exhibit enhanced bactericidal and/or bacteriostatic properties sufficient to retard or inhibit bacterial growth of extrinsically introduced bacteria. Administering an anesthetically effective dose or a sedatively effective dose of a composition of this invention provides a method to reduce the risk of introducing a microbial infection in a patient during a treatment such as may be associated with a surgical procedure, or a procedure designed to ease or relieve pain in a patient or a procedure designed to render a patient unconscious. It can also provide increased patient safety during use and during or associated with repeated use from the same vial of propofol emulsion of this invention such as by repeated puncturing with one or more needles of a seal on a vial containing a composition of this invention, for example in a hospital setting.

It is another advantage that a formulation of a dispersion of propofol of this invention prevents or inhibits growth of bacteria in the formulation and in a vial containing the formulation, and during use in a giving-set linking a vial or syringe acting as a reservoir containing a formulation of this invention via a tube or tubing to a luer connector and thence to a needle positioned in a patient's vein, which giving set is used for administration by injection of a solution or a suspension or a dispersion that comprises the formulation of micromatrices or microdroplets of this invention, diluted or undiluted, during prolonged use and also during repeated use. The bactericidal and/or bacteriostatic properties of a formulation of micromatrices or microdroplets of propofol containing one or more antimicrobial agents in a synergetic amount according to this invention are sufficient to prohibit growth of bacteria present therein such as by extrinsic contamination, and thereby substantially reduce or minimize exposure to bacterial infection to a patient being treated with a propofol formulation of this invention.

It is another advantage that a formulation of this invention can exhibit extended shelf life during use and during repeated use from the same vial by single puncture by a needle or by repeated puncture by a needle during use such as in a clinical setting.

It is another advantage that a formulation of this invention does not cause or exhibit or induce discernable irritation at the site of injection in a patient being treated by injection with a formulation of a dispersion containing propofol according to this invention.

A propofol composition prepared according to this invention and used as an injectable aqueous dispersion of a water-insoluble micromatrix of microdroplets containing propofol and propofol-soluble agents and an antimicrobial agent can substantially limit or inhibit the growth of one or more microorganisms and not irritate the tissue in a patient at the site of injection.

It is an advantage that an aqueous dispersion of propofol of this invention can be prepared as a terminally steam sterilized and stable micromatrix dispersion or microemulsion product in an aqueous medium containing a tonicity modifying amount of a pharmaceutically acceptable hydroxyl-containing excipient such as one or more polyhydroxy compound such as a pharmaceutically acceptable sugar excipient used in intravenous infusion.

It is another advantage of this invention that the stability of a micromatrix dispersion or microdroplet emulsion of a propofol-containing composition is not compromised by the presence of an added antimicrobial agent.

It is yet another advantage that each of such formulations can pass a USP Preservative Effectiveness Test with a level of antimicrobial agent that normally would not provide such protection.

A propofol-containing formulation of this invention can contain a polyhydroxy compound such as a tonicity-modifying amount of one or more sugar or glycerin as an excipient in the aqueous medium of the suspension. A propofol-containing formulation of this invention can exhibit a relatively high viscosity such as from about 1.1 cps to about 8 cps.

Because of reduced lipid content, a formulation of this invention is much less prone to cause hyperlipidemia in human subjects when administered intravenously than a comparable dose of DIPRIVAN. Mixtures of LCT and MCT can undergo rapid metabolic clearance, and their use in the propofol formulations of this invention can be clinically advantageous. Preferred dispersions of micromatrices or microdroplets of propofol of this invention contain mixtures of LCT and MCT and comprise a preferred embodiment of the present invention.

It is another advantage that a composition containing a very high level of propofol, for example up to 7.5% w/w propofol can be provided for multiple use from a single sealed vial and the formulation can be used according to the methods of this invention.

In one embodiment a composition of this invention can comprise of nanometer to micrometer size micromatrices or microdroplets of a water-insoluble micromatrix containing from about 1% up to about 7.5%, preferably from about 1% up to 5% propofol, dispersed in an aqueous phase. The water-insoluble micromatrix consists of the anesthetic propofol with one or more lipophilic agents, i.e., one or more propofol-soluble diluent, dissolved in the propofol at a temperature between about 5° C. to about 90° C. The dispersion of micromatrices or microdroplets can be prepared by homogenization such as by high-pressure homogenization of a mixture of propofol and diluent and an amphiphilic agent in the ratios and amounts cited above. The formulation of the dispersion suspended in an aqueous medium and containing an antimicrobial agent can exhibit anti-microbial activity and can produce no local irritation reaction on injection. The micromatrices or microdroplets preferably have a mean diameter from about 50 nm to about 1000 nm and consist of from 1% to 7.5% of propofol, from 1% to 8% of a propofol-soluble diluent, and about 0.67% to about 5% of a surface stabilizing amphiphilic agent which is preferably a lecithin with the proviso that the ratio of propofol to diluent is in the range of 0.25 to 7.5 while the ratio of propofol to amphiphilic agent is in the range from 0.4 to 1.5.

A composition of the invention can contain a synergetic quantity of one or more pharmaceutically acceptable antimicrobial agent. A composition of the invention can also contain an additional local anesthetic that is optionally also a long acting anesthetic. Additional optional components include lidocaine, a chelating agent, and an antioxidant. In one embodiment, a useful additional antimicrobial agent can be selected from the group consisting of parabens, sulfite ions, metabisulfite ions, edetate, pentetate, and combinations thereof.

A synergetic quantity of antimicrobial agent can be characterized as an amount below the threshold of efficacy of the antimicrobial agent.

In one embodiment, the threshold of efficacy of an antimicrobial agent is defined as the minimum amount of the antimicrobial agent which permits no more than a 0.5 log increase over at least 7 days (168 hours) from the level of an initial inoculum of each of Staphylococcus aureus (ATCC 6538), Escherichia coli (ATCC 8739 and ATCC 8454), Pseudomonas aeruginosa (ATCC 9027), Candida albicans (ATCC 10231), and Aspergillus niger (ATCC 16403) added at approximately 1000 colony forming units (CFU) per milliliter to a reference dispersion at a temperature in the range 20–25° C. To establish a threshold of efficacy of an antimicrobial agent, a washed suspension of each organism is added to a separate aliquot of a homogenized reference dispersion of micromatrices or microdroplets consisting of a propofol-soluble diluent and an amphiphilic agent suspended in an aqueous medium containing a pharmaceutically acceptable water-soluble hydroxyl-group-containing excipient in an amount sufficient to adjust the osmolality of the reference dispersion to be isotonic with blood, the ratio of propofol-soluble diluent to amphiphilic agent being substantially that of the propofol-containing dispersions of this invention. The inoculated reference dispersion is incubated at 20–25° C. for up to 7 days, and viable colonies of the organism are counted at 24 hours after inoculation, at 48 hours after inoculation, and at 7 days or 168 hours after inoculation. A threshold of efficacy can be established by increasing or decreasing the concentration of antimicrobial agent to achieve no more than a 0.5 log increase as described above. Alternatively, the antimicrobial efficacy of an antimicrobial agent at a given concentration can be established on a relative basis by its ability to retard or inhibit microbial growth.

In one aspect of this invention, if the antimicrobial efficacy of a homogenized reference dispersion described above and containing a threshold of efficacy amount of antimicrobial agent is designated $M_{min}$, and if the antimicrobial efficacy of a homogenized reference dispersion described above but containing propofol according to the ratios of ingredients described in this invention and measured as described above for the threshold of efficacy of the antimicrobial agent is designated P, then a dispersion of this invention prepared with a threshold of efficacy amount of the antimicrobial agent should have an antimicrobial efficacy of $P+M_{min}$. However, in this invention the antimicrobial efficacy of the composition is greater than the sum of the efficacies $P+M_{min}$, and a synergetic effect obtains.

In another aspect, synergetic threshold of efficacy can be defined as the amount Mx of an antimicrobial agent that exhibits the expected antimicrobial activity of $P+M_{min}$ in a propofol-containing dispersion of this invention. If a synergy obtains, then Mx is less than $M_{min}$.

In another aspect, synergy in antimicrobial activity between a propofol dispersion and an added synergetic amount of an antimicrobial agent is defined to occur when the combination of the propofol-containing dispersion and the synergetic amount of antimicrobial agent permits no more than a 0.5 log increase from the level of an initial inoculum of each of Staphylococcus aureus (ATCC 6538), Escherichia coli (ATCC 8739 and ATCC 8454), Pseudomonas aeruginosa (ATCC 9027), Candida albicans (ATCC 10231), and Aspergillus niger (ATCC 16403) over at least 7 days (168 hours) when measured by a test wherein a washed suspension of each organism is added to a separate aliquot of the propofol-microdroplet formulation at approximately 1000 colony forming units (CFU) per milliliter at a temperature in the range 20–25° C., incubating at 20–25° C. for up to 7 days, and counting the viable colonies of the organism at 24 hours after inoculation, at 48 hours after inoculation, and at 7 days or 168 hours after inoculation.

It is an integral part of this invention that simultaneous with the synergetic efficacy against microbial growth of the formulation is the maintenance of little or no irritation at the site of injection. Little or no irritation, also referred to as substantially no irritation, is defined by or is evidenced by a test in which the dispersion is administered as a single daily bolus injection over a period of approximately 30 seconds at 12.5 mg/kg of body weight for 3 successive days in the caudal vein of a rat such that a swelling amounting to no more than a 10% increase in the diameter of the rat tail at the site of injection is achieved and maintained at 48 hours post injection of the dispersion.

A useful antimicrobial agent of the present invention can function as a preservative or as an antibacterial agent or as an antifungal agent. In one embodiment, the antimicrobial agent is completely or substantially completely soluble in water. In another embodiment, the antimicrobial agent is partially soluble in water and partially soluble in the microdroplet of propofol and diluent stabilized with an amphiphilic agent. One or a combination of antimicrobial agents can be used.

Antimicrobial agents useful in compositions and methods of this invention can be selected from, but are not limited to, the group consisting of, in alphabetical order, benzalkonium chloride, benzethonium chloride, benzoic acid, benzyl alcohol, butyl paraben, cetylpyridinium chloride, chlorobutanol, chlorocresol, cresol, dehydroacetic acid, ethylparaben, metabisulfite ion, methylparaben, methylparaben sodium, pentetate, phenol, phenylethyl alcohol, potassium benzoate, potassium sorbate, propylparaben, propylparaben sodium, sodium benzoate, sodium dehydroacetate, sodium propionate, sorbic acid, sulfite ion, and thymol, TRIS, and combinations thereof, preferably in pair and triad combinations thereof.

In one embodiment, a preferred antimicrobial agent is benzyl alcohol.

In another embodiment, a preferred antimicrobial agent is sulfite ion.

In another embodiment, a preferred antimicrobial agent is a combination of sulfite ion and edetate.

In a synergetic quantity used in this invention, an antimicrobial agent when tested alone for antimicrobial activity does not meet the Antimicrobial Preservative Effectiveness test that requires efficacy against cultures of each of *Aspergillus niger, Staphyloccus aureus, Escherichia coli, Pseudomonas aeruginosa,* and *Candida albicans* to be evaluated. The concentration of viable bacteria in a formulation must be reduced to not more than 0.1% of the initial inoculation concentration by the fourteenth day. The concentration of a viable yeast and mold must remain at or below the initial inoculation concentration during the first 14 days. The concentration of each test microorganism must remain at or below these designated levels during the remainder of a 28-day test period.

In a preferred embodiment of this invention, the dispersion comprises micromatrices or microdroplets containing propofol and a propofol-soluble diluent having a mean diameter from about 50 nm to about 1000 nm and consisting essentially of about 1% to about 7.5% of propofol, about 1% to about 8% of a propofol-soluble diluent, and about 0.5% to about 5% of a surface stabilizing amphiphilic agent in which the ratio of propofol to diluent is in the range of about 0.25 to about 7.5 while the ratio of propofol to amphiphilic agent is in the range from about 0.4 to about 1.5. Synergetic quantities of one or more antimicrobial agents are present in the dispersion of this invention. A synergetic quantity of antimicrobial agent is preferably between about 0.01% to 0.45% w/v of the propofol dispersion if the antimicrobial agent is selected from the group consisting of benzoic acid, benzyl alcohol, chlorobutanol, chlorocresol, cresol, dehydroacetic acid, phenol, phenylethyl alcohol, potassium benzoate, potassium sorbate, sodium benzoate, sodium dehydroacetate, sodium propionate, sorbic acid, and thymol. A synergetic quantity of antimicrobial agent is preferably between about 0.001% to about 0.01 w/v if the antimicrobial agent is selected from the group consisting of benzalkonium chloride, benzethonium chloride, butyl paraben, cetylpyridinium chloride, ethylparaben, methylparaben, methylparaben sodium, propylparaben, and propylparaben sodium.

All percentages are by weight/volume (w/v) unless otherwise noted.

The ratio of amphiphilic emulsifying agent to propofol and the ratio of diluent to propofol can vary within the limiting ranges of proportional relationships as mentioned previously.

Representative percentage concentrations of propofol and of a propofol-soluble diluent are presented in Table 1. In Table 1, a composition of this invention comprising a micromatrix or microdroplet dispersion containing about 1% to about 7.5% of propofol and about 1% to about 8% of a propofol soluble diluent is in the set of allowable compositions if the ratio of the two ingredients lies within the range between 0.25 (e.g., a composition containing 1% propofol and 4% of a propofol-soluble diluent) to 7.5 (e.g., a composition containing 7.5% propofol and 1% of a propofol-soluble diluent). The final aqueous dispersions of this invention can contain a synergetic quantity of an antimicrobial agent, for example, about 0.01% to 0.45% of an antimicrobial agent selected from the group consisting of benzoic acid, benzyl alcohol, chlorobutanol, chlorocresol, cresol, dehydroacetic acid, phenol, phenylethyl alcohol, potassium benzoate, potassium sorbate, sodium benzoate, sodium dehydroacetate, sodium propionate, sorbic acid, and thymol or about 0.001% to about 0.01 of an antimicrobial agent selected from the group consisting of benzalkonium chloride, benzethonium chloride, butyl paraben, cetylpyridinium chloride, ethylparaben, methylparaben, methylparaben sodium, propylparaben, and propylparaben sodium. Mixtures of antimicrobial agents are useful.

TABLE 1

Allowable percentages of propofol and propofol-soluble diluent and their ratios in the range from 0.25 to 7.5

| Propofol % in final the dispersion | Propofol-soluble diluent (%) in the final dispersion | | | | | | | |
|---|---|---|---|---|---|---|---|---|
| | 1% | 2% | 3% | 4% | 5% | 6% | 7% | 8% |
| | Ratios of Propofol to Propofol-Soluble Diluent | | | | | | | |
| 1% | 1.00 | 0.50 | 0.33 | 0.25 | | | | |
| 2% | 2.00 | 1.00 | 0.67 | 0.50 | 0.40 | 0.33 | 0.29 | 0.25 |
| 3% | 3.00 | 1.50 | 1.00 | 0.75 | 0.60 | 0.50 | 0.43 | 0.38 |
| 4% | 4.00 | 2.00 | 1.33 | 1.00 | 0.80 | 0.67 | 0.57 | 0.50 |
| 5% | 5.00 | 2.50 | 1.67 | 1.25 | 1.00 | 0.83 | 0.71 | 0.63 |
| 6% | 6.00 | 3.00 | 2.00 | 1.50 | 1.20 | 1.00 | 0.86 | 0.75 |
| 7% | 7.00 | 3.50 | 2.33 | 1.75 | 1.40 | 1.17 | 1.00 | 0.88 |
| 7.5% | 7.50 | 3.75 | 2.50 | 1.88 | 1.50 | 1.25 | 1.07 | 0.94 |

TABLE 2

Allowable percentages of propofol and surface stabilizing amphiphilic agent and their ratios in the range is 0.4 to 1.5

| Propofol % in the final dispersion | Surface stabilizing amphiphilic agent (%) in the final dispersion | | | | | | | | |
|---|---|---|---|---|---|---|---|---|---|
| | 0.67% | 1% | 1.5% | 2% | 2.5% | 3% | 3.5% | 4% | 4.5% | 5% |
| | Ratios of Propofol to Surface Stabilizing Amphiphilic Agent | | | | | | | | |
| 1% | 1.50 | 1.00 | 0.67 | 0.50 | 0.40 | | | | | |
| 2% | | | 1.33 | 1.00 | 0.80 | 0.67 | 0.57 | 0.50 | 0.44 | 0.40 |
| 3% | | | | 1.50 | 1.20 | 1.00 | 0.86 | 0.75 | 0.67 | 0.60 |
| 4% | | | | | | 1.33 | 1.14 | 1.00 | 0.89 | 0.80 |

TABLE 2-continued

Allowable percentages of propofol and surface stabilizing amphiphilic agent and their ratios in the range is 0.4 to 1.5

| Propofol % in the final dispersion | Surface stabilizing amphiphilic agent (%) in the final dispersion | | | | | | | | | |
|---|---|---|---|---|---|---|---|---|---|---|
|  | 0.67% | 1% | 1.5% | 2% | 2.5% | 3% | 3.5% | 4% | 4.5% | 5% |
|  | Ratios of Propofol to Surface Stabilizing Amphiphilic Agent | | | | | | | | | |
| 5% |  |  |  |  |  |  | 1.43 | 1.25 | 1.11 | 1.00 |
| 6% |  |  |  |  |  |  |  | 1.50 | 1.33 | 1.20 |
| 7% |  |  |  |  |  |  |  |  |  | 1.40 |
| 7.5% |  |  |  |  |  |  |  |  |  | 1.50 |

Representative percentage concentrations of propofol and of a surface stabilizing amphiphilic agent are presented in Table 2. In Table 2, a composition of this invention comprising a micromatrix or microdroplet dispersion containing about 1% to about 7.5% of propofol and about 0.67% to about 5% of a surface stabilizing amphiphilic agent is in the set of allowable compositions if the ratio of the two ingredients lies within the range between about 0.4 (e.g., a composition containing 1% propofol and 2.5% of a surface stabilizing amphiphilic agent or a composition containing 2% propofol and 5% of a surface stabilizing amphiphilic agent) to about 1.5 (e.g., a composition containing 1% propofol and about 0.67% of a surface stabilizing amphiphilic agent or a composition containing 3% propofol and about 2% of a surface stabilizing amphiphilic agent or a composition containing 6% propofol and about 4% of a surface stabilizing amphiphilic agent or a composition containing about 7.5% propofol and about 5% of a surface stabilizing amphiphilic agent).

In one embodiment, an aqueous dispersion or suspension of micromatrices or microdroplets comprising the anesthetic propofol according to the present invention can contain about 2% propofol, about 1% to about 8% of a propofol-soluble diluent, about 4% to 8% of a tonicity modifying agent in the aqueous medium, about 1.5% to about 5% of an amphiphilic emulsifying agent and about 0.01% to 0.45% of an antimicrobial agent selected from the group consisting of benzoic acid, benzyl alcohol, chlorobutanol, chlorocresol, cresol, dehydroacetic acid, phenol, phenylethyl alcohol, potassium benzoate, potassium sorbate, sodium benzoate, sodium dehydroacetate, sodium propionate, sorbic acid, and thymol.

In another embodiment, an aqueous dispersion or suspension of micromatrices or microdroplets comprising the anesthetic propofol according to the present invention can contain about 2% propofol, about 1% to about 8% of a propofol-soluble diluent, about 4% to 8% of a tonicity modifying agent in the aqueous medium, about 1.5% to about 5% of an amphiphilic emulsifying agent and about 0.001% to about 0.01 of an antimicrobial agent selected from the group consisting of benzalkonium chloride, benzethonium chloride, butyl paraben, cetylpyridinium chloride, ethylparaben, methylparaben, methylparaben sodium, propylparaben, and propylparaben sodium.

In another embodiment of this invention, an aqueous dispersion or suspension of micromatrices or microdroplets comprising the anesthetic propofol according to the present invention can contain about 1% propofol, about 1% to about 4% of a propofol-soluble diluent, about 4% to 8% of a tonicity modifying agent in the aqueous medium, about 0.67% to about 2.5% of an amphiphilic emulsifying agent and about 0.01% to 0.45% of an antimicrobial agent selected from the group consisting of benzoic acid, benzyl alcohol, chlorobutanol, chlorocresol, cresol, dehydroacetic acid, phenol, phenylethyl alcohol, potassium benzoate, potassium sorbate, sodium benzoate, sodium dehydroacetate, sodium propionate, sorbic acid, and thymol.

In another embodiment of this invention, an aqueous dispersion or suspension of micromatrices or microdroplets comprising the anesthetic propofol according to the present invention can contain about 1% propofol, about 1% to about 4% of a propofol-soluble diluent, about 4% to 8% of a tonicity modifying agent in the aqueous medium, about 0.67% to about 2.5% of an amphiphilic emulsifying agent and about 0.001% to about 0.01% of an antimicrobial agent selected from the group consisting of benzalkonium chloride, benzethonium chloride, butyl paraben, cetylpyridinium chloride, ethylparaben, methylparaben, methylparaben sodium, propylparaben, and propylparaben sodium.

In another aspect, an aqueous dispersion of micromatrices or microdroplets of this invention can contain a mixture of about 7.5% of propofol, about 5.4% of anhydrous dextrose dissolved in the aqueous medium, about 5% of polyethoxylated castor oil, and about 0.01% of benzyl alcohol per 100 milliliters of solution wherein a sufficient quantity of water for injection is used to make the balance of the solution.

Preferably, the compositions of the invention are stable to sterilization under pharmaceutically acceptable conditions such as sterilization in a stoppered vial under nitrogen by heating with steam at 121° C. for at least 15 minutes.

Propofol formulations of this invention have hydroxyl-group-containing tonicity modifying compounds in the aqueous medium and can provide compositions of relatively high viscosity. The viscosity of these preparations can be from about 1.1 to 8 cps and more preferably from about 4 to 6 cps. While not adhering to any particular theory, it is believed that such high viscosities may be partly responsible for minimizing the tissue-irritating effect of the formulation.

Stable injectable dispersions of propofol that exhibit a synergetic anti-microbial activity, that have a low lipid content, and that cause low to substantially low zero levels of irritation at the site of injection (i.e., they have no injection site reactivity) can be prepared with little or no phase separation during mixing or storage of the propofol dispersion by application of intense mechanical agitation or high sheer, for example according to the procedures described by Haynes in U.S. Pat. No. 5,637,625 which is incorporated herein by reference.

In a preferred method of preparation of an aqueous dispersion of micromatrices or microdroplets containing propofol and an antimicrobial agent in this invention, an aqueous phase and a lipophilic phase are separately prepared, then are mixed to form a premix suspension, and then are homogenized for example by microfluidization.

A lipophilic phase can be prepared by mixing propofol, one or more propofol-soluble diluent agents, and one or more amphiphilic agents. In one aspect, a substantially uniform lipophilic phase can be formed by dissolution of the propofol-soluble diluent agent and amphiphilic agent in the propofol at ambient temperature or temperatures above body temperature such as above 37° C. The rate of dissolution of the ingredients can be accelerated by heating while mixing with a high-speed homogenizer.

An aqueous phase can be prepared by mixing and dissolving a hydroxyl-group-containing excipient compound and an antimicrobial agent in water such as water for injection.

The lipophilic phase can be added to the aqueous phase or vice versa under agitation with a high-speed homogenizer to form a premix, and the pH can be adjusted to a desired range such as between pH 6 and pH 8.

Alternatively, in another aspect of the process of preparation of a dispersion of this invention, the aqueous phase can additionally contain a well-dispersed phospholipid. The phospholipid can be dispersed in the aqueous phase using a high-speed homogenizer prior to formation of the premix.

Subsequently, the aqueous phase and the lipophilic phase are mixed to form a premix that is then homogenized. Dispersions of the water-insoluble micromatrices or microdroplets of propofol and propofol-soluble diluent in an aqueous medium can be prepared by any of several homogenization methods. For example, dispersions can be prepared by high pressure homogenization of the premix, e.g., by utilizing a Rannie MINI-LAB, type 8.30H Homogenizer, APV Homogenizer Division, St. Paul, Minn. Alternatively, the dispersions can be made by microfluidization of the premix with a Microfluidizer M110EH (Microfluidics, Newton, Mass.). The temperature of the process-fluid during homogenization can rise rapidly because of homogenization impact at a high pressure. High-pressure homogenization at relatively high temperatures (i.e., at a homogenizer inlet temperature above about 30° C. or higher) can result in a dispersion with a tendency to suffer from phase separation. To counter this tendency to separate, the effluent of the homogenizer can be cooled to maintain a useful and acceptable temperature between about 5° C. and 30° C. at the inlet of the homogenizer.

To minimize oxidation of propofol during formation of the micromatrix or microdroplet dispersion, mixing and blending operations as well as vial filing and sealing operations are performed under a generally inert atmosphere, for example under a nitrogen blanket, and the temperature of the steps in the process of formation of the aqueous dispersion is controlled. In a preferred aspect, the temperature is controlled to between about 5° C. and 30° C. to minimize oxidation.

An aqueous dispersion of micromatrices or microdroplets of this invention containing a synergetic quantity of an antimicrobial agent can be filled into a glass vial to about 70–90% volume capacity, purged with a generally inert atmosphere, for example with nitrogen gas, and sealed with a compatible stopper and sealed by methods well known in the pharmaceutical art (e.g., crimp sealing). The thus vialed propofol formulation of this invention can then be steam sterilized according to pharmaceutically acceptable steam sterilization cycles such as heating for 15 minutes at 121° C. followed by cooling to a storage temperature.

A propofol formulation of this invention prepared for example using the method described above can be tested for its ability to cause irritation to venous tissues by intravenous injection in the tail vein of a rat. Female Sprague-Dawley rats, approximately 11 to 12 weeks of age and that weigh between 200 and 250 grams available from Charles River, St. Constant, PQ can be used.

To evaluate tail vein tissue swelling and irritation of a formulation of this invention, a test formulation is administered at time zero on Day 1 as a single bolus injection over a period of approximately 30 seconds in the caudal vein at a site located approximately 5 cm from the distal end of the tail using a propofol dose of 12.5 mg/kg given on the basis of body weight determined on Day 1. A baseline initial circumference measurement of a rat's tail at approximately 2.5 inches proximal to the animal's body is taken prior to the first bolus administration of a test formulation. A second bolus injection is made at time 24 hours on Day 2. Changes in the rat's tail circumference relative to the baseline value are evaluated by comparing measurements taken on Day 2 at time 48 hour and at time 72 hours on Day 3. A nonexistent irritation potential of a composition of this invention is displayed by a zero increase in the tail circumference upon caudal vein intravenous administration. Acceptable levels of irritation which are substantially zero are displayed by between zero and 10% increase, preferably between zero and 5% increase in the tail circumference upon caudal vein intravenous administration.

In addition, each rat used in the above experiment is observed during and after the injection. The time required for loss of consciousness (induction time) is recorded. Useful induction times range from about 20 seconds to about one minute when a dose of about 12.5 mg/kg as a single bolus intravenous injection of a formulation of this invention is given to rats. The time to recover (righting response time) indicated by spontaneous attempts to stand up on four feet is also measured. Useful righting time responses are from about 10 to about 20 seconds. The duration of anesthesia is measured as the difference between the time when righting response occurs minus the time when consciousness is lost.

A useful formulation of this invention that provides enhanced antimicrobial activity and minimum irritate on injection can comprise propofol at about 1% (w/w), plus LIPOID E80 at about 1% (w/w) plus 1,2-dimyristoyl-sn-glycero-3-[phospho-rac-(1-glycerol)] (DMPG) at about 0.25% (w/w) plus ethyl oleate at about 3.75% together with an antimicrobial agent in amounts described above.

The dispersions of this invention are nonpyrogenic and are suitable for intravenous administration for use in the induction and maintenance of anesthesia or sedation. Intravenous injection in the arm of a patient of a therapeutic dose of a dispersion of this invention containing propofol produces hypnosis rapidly with minimal excitation, preferably within 40 seconds from the start of an injection, i.e., within the time for one arm to brain circulation. Dose amounts useful to induce anesthesia or sedation and to maintain a state of anesthesia or sedation are well known for propofol in the form of DIPRIVAN and can vary with the patient's age and duration of use of the drug. A typical dose level of use of the dispersions of this invention is an amount of dispersion that will provide about 2 to 2.5 mg/kg of propofol to an adult patient under 55 years of age for induction of general anesthesia when unpremedicated or when premedicated for example with oral benzodiazepines or intramuscular opioids. The dispersion should be titrated (approximately 40 mg every 10 seconds) against the response of the patient until the clinical signs show the onset of anesthesia. More elderly patients can require less drug such as about 1 to 1.5 mg/kg for induction of anesthesia. Other dose levels of propofol are well known and are described in the Physicians Desk Reference, 1999 under DIPRIVAN.

In-vitro evaluation of the hemolytic influence of the preparations of this invention on human whole blood is determined as a further guide to selecting formulations with a low tendency to produce irritation around the site of injection. The hemolytic potential of a formulation on blood is evaluated by an assay of erythrocyte cytoplasmic marker enzyme, lactate dehydrogenase (LDH) which escapes from the leaky or ruptured erythrocytes into the plasma compartment of the blood. For the assay, blood is obtained from male or female Caucasian human volunteers of 18 to 65 years of age and stabilized with sodium heparin. A test formulation is mixed with an equal volume of human whole blood and incubated at 37° C. for about 1 hour. The mixture is then held at ambient temperature for 30 minutes followed by centrifugation at 1500 rpm for 10 min. The level of LDH in the supernatant is determined according to protocols known in the art. An upper limit titre is determined by measuring the LDH levels resulting from hemolysis by amiodarone hydrochloride, a compound known to result in vein irritation upon venous injection in clinical settings (PDR 1999, p. 3289). Amiodarone hydrochloride IV solution, when tested at 50 mg/mL and after dilution with 5% aqueous dextrose to 1.8 mg/mL can result in LDH values of about 8000 IU/L and about 700 IU/L, respectively.

The compositions of the present invention can be tested for their ability to inhibit the growth of microorganisms that are potential source of most likely infections in the clinical situation. Growth of *Staphylococcus aureus* (ATCC 6538), *Escherichia coli* (ATCC 8739 and ATCC 8454), *Pseudomonas aeruginosa* (ATCC 9027), *Candida albicans* (ATCC 10231), and *Aspergillus niger* (ATCC 16403) can be measured by a test wherein a washed suspension of each organism is added to a separate aliquot of a composition of this invention at approximately 1000 colony forming units (CFU) per mL, at a temperature in the range 20–25° C. The inoculated mixtures can be incubated at 20–25° C. The viability of the microorganisms in the inoculated formulation can be determined by counting the colonies of viable organisms at 24 hours, at 48 hours, at 72 hours, at 96 hours, at 120 hours, at 144 hours, at 168 hours (i.e., at 7 days) or at other suitable times after inoculation.

Compositions of this invention are substantially non-irritating at the site of injection when evaluated in a rat tail test and in an LDH activity test and liberate less than 1000 iu/L of LDH in blood.

Compositions of this invention can provide a clinically effective amount of propofol in bolus intravenous injection or infusion. Compositions of this invention do not have an excessive amount of oils or triglycerides and thus reduce the propensity of a patient to fall victim to hyperlipidemia. Compositions of this invention cause substantially no irritation at the site of injection. Compositions of this invention have sufficient bactericidal or bacteriostatic property to provide enhanced patient safety and extended shelf life during single bolus use, during multiple bolus use, and during prolonged infusion use in a clinical setting.

Useful compositions of this invention can be prepared to contain propofol from 1% to about 7.5%, preferably from 2% to 5.0%.

Useful compositions of this invention can be terminally steam sterilizable without destabilization.

An example of a useful composition of this invention that contains 1% propofol and a synergetic quantity of an antimicrobial agent as described above contains about 0.8% of DMPC (dimyristoylphosphatidylcholine) plus about 0.1% of DMPG (dimyristoylphosphatidylglycerol) and about 2% M810 (MIGLYOL-810) in an aqueous medium containing about 2.5% glycerin. Another example of a useful composition of this invention that contains 1% propofol and a synergetic quantity of an antimicrobial agent as described above contains about 1% of LIPOID E80 plus 0.25% of DMPG and about 8% of ethyl oleate in an aqueous medium containing about 2.5% glycerin.

An example of a useful composition of this invention that contains 2% propofol and a synergetic quantity of an antimicrobial agent as described above contains about 1.6% LIPOID E80 and about 4% ethyl oleate in an aqueous medium containing about 7.5% mannitol. Another example of a useful composition of this invention that contains 2% propofol and a synergetic quantity of an antimicrobial agent as described above contains about 1.6% LIPOID E80 plus 1.6% EPC (egg phosphatidylcholine) plus 0.05% DMPG and about 4% ethyl oleate in an aqueous medium containing about 2.5% glycerin. Another example of a useful composition of this invention that contains 2% propofol and a synergetic quantity of an antimicrobial agent as described above contains about 1.6% LIPOID E80 plus 0.1% DMPG and about 4% soybean oil in an aqueous medium containing about 2.5% glycerin. Another example of a useful composition of this invention that contains 2% propofol and a synergetic quantity of an antimicrobial agent as described above contains about 1.6% LIPOID E80 plus 0.1% DMPG and about 6% ethyl oleate in an aqueous medium containing about 2.5% glycerin. Another example of a useful composition of this invention that contains 2% propofol and a synergetic quantity of an antimicrobial agent as described above contains about 1.6% LIPOID E80 plus 0.1% DMPG and about 4% ethyl oleate in an aqueous medium containing about 2.5% glycerin. Another example of a useful composition of this invention that contains 2% propofol and a synergetic quantity of an antimicrobial agent as described above contains about 2% LIPOID E80 plus 0.1% DMPG and about 4% MIGLYOL-810 in an aqueous medium containing about 2.5% glycerin. Another example of a useful composition of this invention that contains 2% propofol and a synergetic quantity of an antimicrobial agent as described above contains about 2.4% LIPOID E80 plus 0.15% DMPG and about 4% soybean oil in an aqueous medium containing about 7.5% mannitol. Another example of a useful composition of this invention that contains 2% propofol and a synergetic quantity of an antimicrobial agent as described above contains about 3% LIPOID E80 plus 0.15% DMPG and about 4% ethyl oleate in an aqueous medium containing about 20% trehalose. Another example of a useful composition of this invention that contains 2% propofol and a synergetic quantity of an antimicrobial agent as described above contains about 1.6% EPL (egg phospholipids) plus 0.05% DMPG and about 4% MIGLYOL-810 in an aqueous medium containing about 5.5% mannitol. Another example of a useful composition of this invention that contains 2% propofol and a synergetic quantity of an antimicrobial agent as described above contains about 1.6% EPL and about 4% MIGLYOL-810 in an aqueous medium containing about 5.5% mannitol. Another example of a useful composition of this invention that contains 2% propofol and a synergetic quantity of an antimicrobial agent as described above contains about 1.6% EPL and about 4% ethyl oleate in an aqueous medium containing about 7.5% mannitol. Another example of a useful composition of this invention that contains 2% propofol and a synergetic quantity of an antimicrobial agent as described above contains about 1.6% EPL and about 4% MIGLYOL-810 in an aqueous medium containing about 2.5% glycerin. Another example of a useful composition of this invention that contains 2% propofol and a synergetic quantity of an antimicrobial agent as described above contains about 1.6% EPL plus about 0.1% DMPG and about 6% soybean oil in an aqueous medium containing about 2.5% glycerin. Another example of a useful composition of this invention that contains 2% propofol and a synergetic quantity of an antimicrobial agent as described above contains about 1.6% EPL plus about 0.05% DMPG and about 4% MIGLYOL-810 in an aqueous medium containing about 2.5% glycerin. Another example of a useful composition of this invention that contains 2% propofol and a synergetic quantity of an antimicrobial agent as described above contains about 2.2% SPC (soy phosphatidylcholine) plus about 0.15% DMPG and about 4% soybean oil in an aqueous medium containing about 5.5% mannitol. Another example of a useful composition of this invention that contains 2% propofol and a synergetic quantity of an antimicrobial agent as described above contains about 2% SPC plus about 0.5% SSPC (saturated soy phosphatidylcholine) plus about 0.05% DMPG and about 4% soybean oil in an aqueous medium containing about 5.5% mannitol.

A preferred composition of this invention that contains 2% propofol and a synergetic quantity of an antimicrobial agent as described above also contains about 1.6% egg phosphatidylcholine plus about 0.1% dimyristoylphosphatidylglycerol plus about 6% MIGLYOL-810 in an aqueous medium containing about 12.5% trehalose.

Another preferred composition of this invention that contains 2% propofol and a synergetic quantity of an antimicrobial agent as described above also contains about 2% soy phosphatidylcholine plus about 0.5% saturated soy phosphatidylcholine plus about 0.05% dimyristoylphosphatidylglycerol and about 4% MIGLYOL-810 in an aqueous medium containing about 5.5% mannitol.

Propofol formulations of this invention are useful for production and maintenance of ambulatory anesthesia, neurosurgical anesthesia, and pediatric anesthesia; for monitored anesthesia care; for intensive care sedation; for sedation, for treatment of migraine headaches, as antiemetics, as well as other clinical uses.

The dispersions of propofol of the present invention are rapidly effective in bolus form and useful for induction of anesthesia. The dispersions of the present invention can also be administered by repeated small doses or by continuous infusion or by semi-continuous infusion, and are effective for maintaining anesthesia. In one embodiment of the invention, the anesthetic is administered parenterally to induce anesthesia and then to maintain anesthesia. Preferably, an effective amount of a dispersion administered to a patient provides propofol at an initial rate of about 2.0 mg/kg (milligrams per kilogram) body weight of the patient. For maintenance of anesthesia, an effective amount of a dispersion is administered at slower rates such as at about 0.2 mg/kg/min. During the time of administration, and during a repeated or prolonged (e.g. from 0.1 hour up to 6 hours, or from 0.1 hour up to 12 hours, or from 0.1 hour up to 24 hours, or from 0.1 hour up to about 7 days) administration such as by using repeated (e.g. 1, 2, 3, 4 or more up to about 10) punctures of the seal on a vial of a dispersion of this invention, the synergetic antimicrobial activity of the propofol dispersion and the antimicrobial agent maintains acceptably low levels of microbial content in the vial and in the apparatus such as a needle and tubing (sometimes referred to as giving sets) used for administration of the dispersion to the patient. The dispersions of this invention provide a method of reducing the risk of infection in a patient when administered over a long period of time or when administered using multiple punctures of a seal on a vial of the dispersion.

In one aspect, an effective amount of a dispersion of this invention contains a dosage level of propofol for maintenance of anesthesia of about 4 to 12 mg/kg/hour. In another aspect, an effective amount of a dispersion of this invention contains a dosage level of propofol to achieve a sedative effect of about 0.25 to about 5 mg/kg/hour.

A dispersion containing propofol and antimicrobial agent of the present invention can be short acting and has a smooth induction with substantially zero amount of pain on intravenous injection or infusion.

The amount of antimicrobial agent present in the dispersion is small and will not destabilize the suspension or dispersion and thus allows for prolonged storage of the dispersion prior to use. Charged antimicrobial agents are used in amounts small enough to avoid destabilization of the dispersion as would be the case in the presence of higher concentrations with higher ionic strength or ionic load.

It can be seen that this invention is one that is well adapted to attain all the ends and objects hereinabove set forth together with other advantages which are obvious and inherent to the formulation. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limited sense.

What is claimed is:

1. A sterile, injectable dispersion of micromatrices or microdroplets having a mean diameter from about 50 nm to about 1000 nm comprising:
   propofol in an amount of from about 1% to about 7.5% by weight/volume of the dispersion,
   a propofol-soluble diluent in an amount of from about 1% to about 8% by weight/volume of the dispersion, and
   a surface stabilizing amphiphilic agent in an amount of from about 0.67% to about 5% by weight/volume of the dispersion, suspended in an aqueous medium containing
      a synergetic quantity of antimicrobial agent and
      a tonicity modifying amount of a pharmaceutically acceptable water-soluble hydroxyl-group-containing excipient,
   wherein the ratio of propofol to diluent is in the range of about 0.25 to about 7.5, and the ratio of propofol to amphiphilic agent is in the range from about 0.4 to about 1.5.

2. The dispersion of claim 1, wherein the diluent is selected from the group consisting of a C-2 to C-24 saturated fatty acid C-2 to C-24 alcohol ester, a C-8 to C-24 unsaturated fatty acid C-2 to C-24 alcohol ester, saturated and unsaturated naturally available and pharmaceutically acceptable hydrocarbons and hydrocarbon alcohols having from 15 to 35 carbon atoms, triglycerides of medium chain C-8 to C-12 saturated and unsaturated pharmaceutically acceptable fatty acids, triglycerides of long chain C-14 to C-30 saturated and unsaturated pharmaceutically acceptable fatty acids, a pharmaceutically acceptable oil from a vegetable or fish, and mixtures thereof.

3. The dispersion of claim 2, wherein the oil is selected from the group consisting of soybean oil, safflower oil, cottonseed oil, corn oil, sunflower oil, arachis oil, castor oil, olive oil, and coconut oil, omega-3 polyunsaturated oils, omega-3 marine triglycerides, and combinations thereof.

4. The dispersion of claim 1, wherein the diluent is selected from the group consisting of isopropyl myristate, isopropyl palmitate, cholesteryl oleate, ethyl oleate, palmitoyl acetate, squalene, squalane, MIGLYOL 810, capric-caprylic triglyceride, soybean oil, and mixtures thereof.

5. The dispersion of claim 1, wherein the amphiphilic agent is selected from the group consisting of pharmaceutically acceptable phospholipids, pharmaceutically acceptable lecithins, and mixtures thereof.

6. The dispersion of claim 1, wherein the amphiphilic agent is selected from the group consisting of egg lecithin, egg phosphatidylcholine, soy lecithin, soy phosphatidylcholine, 1,2-dimyristoyl-sn-glycero-3-phosphotidlycholine (DMPC), 1,2-dimyristoyl-sn-glycero-3-[phospho-rac-(1-glycerol)] (DMPG), L-alpha-phosphatidylcholine, palmitoyl-linoleoyl phosphatidylcholine, stearoyl-linoleoyl phosphatidylcholine, lysolecithin, phosphatidic acid, phosphatidyl-DL-glycerol, phosphatidylethanolamine, palmitoyl-oleoyl phosphatidylcholine, phosphatidylinositol, phosphatidylserine, 1,3-bis(sn-3-phosphatidyl)-sn-glycerol, 1,3-di(3-sn-phosphatidyl)-sn-glycerol, and mixtures thereof.

7. The dispersion of claim 1, wherein the amphiphilic agent comprises a surfactant selected from the group consisting of a pharmaceutically acceptable non-ionic surfactant, a pharmaceutically acceptable ionic surfactant, and mixtures thereof.

8. The dispersion of claim 1, wherein the hydroxyl-group-containing excipient is selected from the group consisting of a monosaccharide, a disaccharide, a trisaccharide, sucrose, dextrose, trehalose, mannitol, lactose, glycerol, glycerin, sorbitol, and mixtures thereof.

9. The dispersion of claim 1, wherein the antimicrobial agent is selected from the group consisting of benzoic acid, benzyl alcohol, chlorobutanol, chlorocresol, cresol, dehydroacetic acid, phenol, phenylethyl alcohol, potassium benzoate, potassium sorbate, sodium benzoate, sodium dehydroacetate, sodium propionate, sorbic acid, and thymol, and mixtures thereof.

10. The dispersion of claim 1, wherein the antimicrobial agent is selected from the group consisting of benzalkonium chloride, benzethonium chloride, butyl paraben, cetylpyridinium chloride, ethylparaben, methylparaben, methylparaben sodium, propylparaben, and propylparaben sodium, and mixtures thereof.

11. The dispersion of claim 1, wherein propofol is present in an amount of from about 2% to about 5%.

12. The dispersion of claim 11, wherein propofol is present in an amount of about 2%.

13. The dispersion of claim 1, wherein the hydroxyl-group-containing excipient is mannitol.

14. The dispersion of claim 13, wherein mannitol is present in an amount of from about 5.5% to about 7.5%.

15. The dispersion of claim 14, wherein mannitol is present in an amount of about 5.5%.

16. The dispersion of claim 1, wherein the propofol-soluble diluent is a medium chain triglyceride.

17. The dispersion of claim 16, wherein the medium chain triglyceride is a triglyceride of a C-8 to C-12 saturated or unsaturated pharmaceutically acceptable fatty acid.

18. The dispersion of claim 17, wherein the medium chain triglyceride is capric-caprylic triglyceride.

19. The dispersion of claim 18, wherein the medium chain triglyceride is MIGLYOL 810.

20. The dispersion of claim 16, wherein the medium chain triglyceride is present in an amount of from about 1% to about 4%.

21. The dispersion of claim 20, wherein the medium chain triglyceride is present in an amount of from about 2% to about 4%.

22. The dispersion of claim 21, wherein the medium chain triglyceride is present in an amount of about 4%.

23. The dispersion of claim 1, wherein the amphiphilic agent is egg lecithin.

24. The dispersion of claim 23, wherein the egg lecithin is present in an amount of from about 1.5% to about 5%.

25. The dispersion of claim 24, wherein the egg lecithin is present in an amount of from about 0.67% to about 2.5%.

26. The dispersion of claim 25, wherein the egg lecithin is present in an amount of about 1.6%.

27. The dispersion of claim 1, which includes anionic dimyristoylphosphatidyl glycerol.

28. The dispersion of claim 27, wherein the anionic dimyristoylphosphatidyl glycerol is present in an amount of 0.05% to 0.25%.

29. The dispersion of claim 28, wherein the anionic dimyristoylphosphatidyl glycerol is present in an amount of 0.1%.

30. The dispersion of claim 1, which includes egg lecithin and anionic dimyristoylphosphatidyl glycerol.

31. The dispersion of claim 30, wherein the egg lecithin is present in an amount of about 1.5% to about 5% and the anionic dimyristoylphosphatidyl glycerol is present in an amount of 0.05% to 0.25%.

32. The dispersion of claim 31, wherein the egg lecithin is present in an amount of about 1.6% and the anionic dimyristoylphosphatidyl glycerol is present in an amount of 0.1%.

33. The dispersion of claim 1, wherein the pH of the dispersion is from about 5 to about 9.

34. The dispersion of claim 33, wherein the pH of the dispersion is from about 5 to about 8.

35. The dispersion of claim 34, wherein the pH of the dispersion is from about 6 to about 8.

36. The dispersion of claim 1, wherein the dispersion is sealed in a vial under nitrogen.

37. The dispersion of claim 36, wherein the vial is sealed with a stopper.

38. The dispersion of claim 1, wherein the synergetic quantity of antimicrobial agent is about 0.01% to 0.45% w/v of propofol.

39. The dispersion of claim 1, wherein the antimicrobial agent is benzyl alcohol.

40. The dispersion of claim 39, wherein the synergetic quantity of benzyl alcohol is about 0.01% to 0.45% w/v of propofol.

41. The dispersion of claim 1, wherein the synergetic quantity of antimicrobial agent is about 0.001% to about 0.01% w/v of propofol.

42. The dispersion of claim 1, wherein the antimicrobial agent is EDTA.

43. The dispersion of claim 1, wherein the synergistic quantity of antimicrobial agent is an amount of antimicrobial agent that permits no more than a 0.5 log increase over at least 7 days from the level of an initial inoculum of each of *Staphylococcus aureus, Escherichia coli, Pseudomonas aeruginosa, Candida albicans*, and *Aspergillus niger* added at approximately 1000 colony forming units per milliliter to a reference dispersion at a temperature in the range of 20–25° C.

44. The dispersion of claim 1, wherein the viscosity of the dispersion is in the range from about 1.1 to 8 cps at ambient temperature.

45. The dispersion of claim 1, wherein the viscosity of the dispersion is in the range from about 1.1 to 8 cps at a temperature range from 20–25° C.

46. A sterile, injectable dispersion of micromatrices or microdroplets having a mean diameter from about 50 nm to about 1000 nm comprising:
  propofol in an amount of from about 1% to about 7.5% by weight/volume of the dispersion,
  a medium chain triglyceride of a C-8 to C-12 saturated or unsaturated pharmaceutically acceptable fatty acid in an amount of from about 1% to about 8% by weight/volume of the dispersion, and
  a surface stabilizing amphiphilic agent in an amount of from about 0.67% to about 5% by weight/volume, suspended in an aqueous medium containing
    a synergetic quantity of antimicrobial agent and
    a tonicity modifying amount of a pharmaceutically acceptable water-soluble hydroxyl-group-containing excipient,
  wherein the ratio of propofol to diluent is in the range of about 0.25 to about 7.5, and the ratio of propofol to amphiphilic agent is in the range of about 0.4 to about 1.5.

47. A sterile, injectable dispersion of micromatrices or microdroplets having a mean diameter from about 50 nm to about 1000 nm comprising:
  propofol in an amount of about 2% by weight/volume of the dispersion,
  a medium chain triglyceride of a pharmaceutically acceptable fatty acid in an amount of about 4% by weight/volume of the dispersion,
  egg lecithin in an amount of about 1.6% by weight/volume of the dispersion, and
  anionic dimyristoylphosphatidyl glycerol in an amount of 0.1% by weight/volume of the dispersion, suspended in an aqueous medium containing
    a synergetic quantity of antimicrobial agent and
    a tonicity modifying amount of a pharmaceutically acceptable water-soluble hydroxyl-group-containing excipient,
  wherein the ratio of propofol to diluent is in the range of about 0.25 to about 7.5, and the ratio of propofol to amphiphilic agent is in the range of about 0.4 to about 1.5.

48. A sterile, injectable dispersion of micromatrices or microdroplets having a mean diameter from about 50 nm to about 1000 nm comprising:
  propofol in an amount of about 1% by weight/weight of the dispersion,
  egg lecithin in an amount of about 1% by weight/weight of the dispersion,
  anionic dimyristoylphosphatidyl glycerol in an amount of about 0.25% by weight/weight of the dispersion, and
  ethyl oleate in an amount of about 3.75%, suspended in an aqueous medium containing
    a synergetic quantity of antimicrobial agent and
    a tonicity modifying amount of a pharmaceutically acceptable water-soluble hydroxyl-group-containing excipient,
  wherein the weight ratio of propofol to diluent is in the range of about 0.25 to about 7.5, and the weight ratio of propofol to amphiphilic agent is in the range of about 0.4 to about 1.5.

* * * * *